(12) United States Patent
Shone et al.

(10) Patent No.: US 7,470,661 B2
(45) Date of Patent: Dec. 30, 2008

(54) DELIVERY OF SUPEROXIDE DISMUTASE TO NEURONAL CELLS

(75) Inventors: Clifford Charles Shone, Salisbury (GB); John Mark Sutton, Salisbury (GB); Bassam Hallis, Salisbury (GB); Nigel Silman, Salisbury (GB)

(73) Assignee: Syntaxin Limited, Salisbury, Wiltshire (GB)

( * ) Notice: Subject to any disclaimer, the term of this patent is extended or adjusted under 35 U.S.C. 154(b) by 373 days.

(21) Appl. No.: 11/062,471

(22) Filed: Feb. 22, 2005

(65) Prior Publication Data

US 2005/0255093 A1 Nov. 17, 2005

Related U.S. Application Data

(63) Continuation of application No. 09/831,050, filed as application No. PCT/GB99/03699 on Nov. 5, 1999, now abandoned.

(30) Foreign Application Priority Data

Nov. 5, 1998 (GB) ................... 9824282.9

(51) Int. Cl.
*A61K 38/00* (2006.01)
*A61K 38/16* (2006.01)
*A61K 38/43* (2006.01)
*C07K 14/00* (2006.01)
*C12N 9/00* (2006.01)

(52) U.S. Cl. .............................. 514/2; 514/6; 424/94.1; 530/350; 530/402; 435/183

(58) Field of Classification Search ........................ None
See application file for complete search history.

(56) References Cited

U.S. PATENT DOCUMENTS

| | | | |
|---|---|---|---|
| 5,436,162 A * | 7/1995 | Heckl et al. | 435/320.1 |
| 5,780,024 A | 7/1998 | Brown et al. | |
| 5,989,545 A | 11/1999 | Foster et al. | |
| 6,395,513 B1 | 5/2002 | Foster et al. | |
| 6,461,617 B1 | 10/2002 | Shone et al. | |
| 6,632,440 B1 | 10/2003 | Quinn et al. | |
| 2003/0049264 A1 | 3/2003 | Foster et al. | |
| 2003/0147895 A1 | 8/2003 | Shone et al. | |
| 2003/0166238 A1 | 9/2003 | Shone et al. | |
| 2004/0071736 A1 | 4/2004 | Quinn et al. | |

FOREIGN PATENT DOCUMENTS

WO WO 00/28041 5/2000

OTHER PUBLICATIONS

Yokasawa, et al, 1989, Infection and Immunity, 57(1): 272-277.*
Hunter, et al, 1997, J. Biol. Chem. 272(46): 28652-28659.*
White, J.A. & Scandalios, J.G., 1989, Proc. Natl. Acad. Sci, 86: 3534-3538.*

Application and Prosecution History for "Recombinant Toxin Fragments," Shone et al., U.S. Appl. No. 09/255,829, filed Feb. 23, 1999.
Application and Prosecution History for "Conjugates of Galatose-Binding Lectins and Clostridial Neurotoxins as Analgesics," Duggan et al., U.S. Appl. No. 09/529,130, with a §371 date Jun. 22, 2000.
Application and Prosecution History for "Methods and Compounds for the Treatment of Mucus Hypersecretion," Quinn et al., U.S. Appl. No. 09/763,669, with a §371 date May 29, 2001.
Application and Prosecution History for "Delivery of Superoxide Dismutase to Neuronal Cells," Shone et al., U.S. Appl. No. 09/831,050, with a §371 date of Aug. 20, 2001.
Application and Prosecution History for "Constructs for Delivery of Therapeutic Agents to Neuronal Cells," Shone et al., U.S. Appl. No. 10/130,973, with a §371 date of Jun. 25, 2002.
Application and Prosecution History for "Recombinant Toxin Fragments," Shone et al., U.S. Appl. No. 10/241,596, filed Sep. 12, 2002.
Application and Prosecution History for "Methods and Compounds for the Treatment of Mucus Hypersecretion," Quinn et al., U.S. Appl. No. 10/633,698, filed Aug. 5, 2003.
Shone et al., "Recombinant Toxin Fragments," U.S. Appl. No. 11/077,550, filed Mar. 11, 2005.
Shone et al., "Recombinant Toxin Fragments," U.S. Appl. No. 10/527,411, filed Mar. 11, 2005.
Bowler, C., et al., "Characterization of the *Bacillus stearothermophilus* Manganese Superoxide Dismutase Gene and Its Ability to Complement Copper/Zinc Superoxide Dismutase Deficiency in *Saccharomyces cerevisiae*," *Journal of Bacteriology* 172:1539-1546, American Society for Microbiology (1990).
Brock, C.J., and Walker, J.E., "Superoxide Dismutase from *Bacillus stearothermophilus*. Complete Amino Acid Sequence of a Manganese Enzyme," *Biochemistry* 19:2873-2882, American Chemical Society (1980).
Chambers, S.P., et al., "Physical characterization and over-expression of the *Bacillus caldotenax* superoxide dismutase gene," *FEMS Microbiol. Lett. 91*:277-284, Elsevier Science Publishers B.V. (1992).
Cuevas, P., et al., "Ischemic Reperfusion Injury in Rabbit Spinal Cord: Protective Effect of Superoxide Dismutase on Neurological Recovery and Spinal Infarction," *Acta. Anat. 137*:303-310, Karger AB, Basel (1990).
de Paiva, A. and Dolly, J.O., "Light chain of botulinum neurotoxin is active in mammalian motor nerve terminals when delivered via liposomes," *FEBS. Lett. 277*:171-174, Elsevier Science Publishers B.V. (1990).

(Continued)

*Primary Examiner*—Elizabeth C. Kemmerer
*Assistant Examiner*—Sandra Wegert
(74) *Attorney, Agent, or Firm*—Sterne, Kessler, Goldstein & Fox PLLC

(57) ABSTRACT

A composition for delivery of superoxide dismutase to neuronal cells comprise a superoxide dismutase linked by a linker to a neuronal cell targeting component, which component comprises a first domain that binds to a neuronal cell and a second domain that translocates the superoxide dimutase into the neuronal cell. After translocation, the linker is cleaved to release superoxide dimutase from the neuronal cell targeting domain. Also described is use of the composition for treatment of oxidative damage to neuronal cells and further targeting of the composition using human mitochondrial leader sequences. A hybrid polypeptide is described that contains a bacterial superoxide dismutase plus a sequence that targets a human mitochondira.

5 Claims, 4 Drawing Sheets

OTHER PUBLICATIONS

Figure 3:
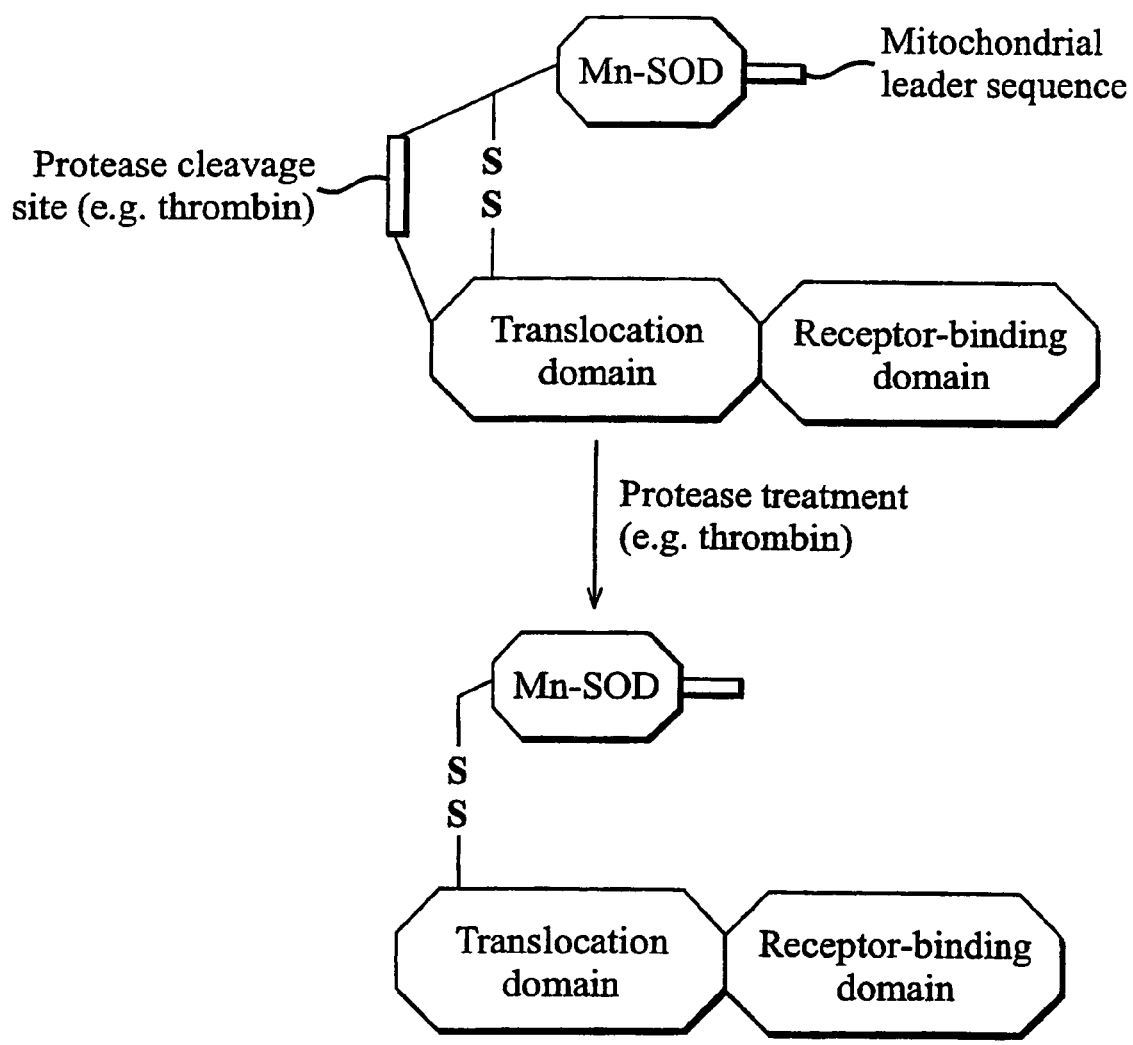

Dolly, J.O., et al., "Acceptors for botulinum neurotoxin reside on motor nerve terminals and mediate its internalization," *Nature* 307:457-460, Macmillan Journals (1984).

Evans, D.M., et al., "Botulinum neurotoxin type B. Its purification, radioiodination and interaction with rat-brain synaptosomal membranes," *Eur. J. Biochem.* 154:409-416, Springer International (1986).

Figueiredo, D.M., et al., "Delivery of recombinant tetanus-superoxide dismutase proteins to central nervous system neurons by retrograde axonal transport," *Exp. Neurol.* 145:546-554, Academic Press (1997).

Francis, J.W., et al., "Cu/Zn Superoxide Dismutase (SOD-1): Tetanus Toxin Fragment C Hybrid Protein for Targeted Delivery of SOD-1 to Neuronal Cells," *J. Biol. Chem.* 270:15434-15442, American Society for Biochemistry and Molecular Biology, Inc. (1995).

Francis, J.W., et al., "Postischemic Infusion of Cu/Zn Superoxide Dismutase or SOD:Tet451 Reduces Cerebral Infarction Following Focal Ischemia/Reperfusion in Rats," *Exp. Neurol.* 146:435-443, Academic Press (1997).

Fujii, J., et al., "A Defect in the Mitochondrial Import of Mutant Mn-Superoxide Dismutase Produced in Sf21 Cells," *J. Biochem.* 124:340-346, Japanese Biochemical Society (1998).

Keller, J.N., et al., "Mitochondrial Manganese Superoxide Dismutase Prevents Neural Apoptosis and Reduces Ischemic Brain Injury: Suppression of Peroxynitrite Production, Lipid Peroxidation and Mitochondrial Dysfunction," *J. Neurosci.* 18:687-697, Society for Neuroscience (1998).

L'Abbe, M.R., and Trick, K.D., "Changes in Pancreatic Glutathione Peroxidase and Superoxide Dismutase Activities in the Prediabetic Diabetes-Prone BB Rat," *Proc. Soc. Exp. Biol. Med.* 207:206-212, Society for Experimental Biology and Medicine (1994).

Lebovitz, R.M., et al., "Neurodegeneration, myocardial injury, and perinatal death in mitochondrial superoxide dismutase-deficient mice," *Proc. Natl. Acad. Sci. U.S.A.* 93:9782-9787, National Academy of Sciences (1996).

Lim, K.H., et al., "Prevention of Reperfusion Injury of Ischemic Spinal Cord: Use of Recombinant Superoxide Dismutase," *Ann. Thorac. Surg.* 42:282-286, Presented at the Thirty-Third Annual Meeting of the Southern Thoracic Surgical Association, Oct. 30-Nov. 1, (1986).

Matsumiya, N., et al., "Conjugated Superoxide Dismutase Reduces Extent of Caudate Injury After Transient Focal Ischemia in Cats," *Stroke* 22:1193-1200, American Heart Association (1991).

Mattson, M.P., et al., "Calcium, Free Radicals, and Excitotoxic Neuronal Death in Primary Cell Culture," in *Methods in Cell Biology*, Schwartz, L.M. and B.A. Osborne, eds., Academic Press, San Diego, CA, vol. 46, pp. 187-216 (1995).

McInnes, C., and Dolly, J.O., "$Ca^{2+}$-dependent noradrenaline release from permeabilised PC12 cells is blocked by botulinum neurotoxin A or its light chain," *FEBS Lett.* 261:323-326, Elsevier Science Publishers B.V. (1990).

Musser, D.A., and Oseroff, A.R., "The Use of Tetrazolium Salts To Determine Sites Of Damage To the Mitochondrial Electron Transport Chain In Intact Cells Following In Vitro Photodynamic Therapy With Photofrin II," *Photochem. Photobiol.* 59:621-626, American Society for Photobiology (1994).

Nishida, T., et al., "The serum level of manganese superoxide dismutase in patients with ovarian epithelial malignancy," *Oncol. Reports* 2:643-646, Current Science, Inc. (1995).

Prodromou, C., and Pearl, L.H., "Recursive PCR: a novel technique for total gene synthesis," *Protein Engineering* 5:827-829, Oxford University Press (1992).

Shone, C.C., et al., "Inactivation of *Clostridium botulinum* type A neurotoxin by trypsin and purification of two tryptic fragments. Proteolytic action near the COOH-terminus of the heavy subunit destroys toxin-binding activity," *Eur. J. Biochem.* 151:75-82, Springer International (1985).

Shone, C.C., "Understanding toxin action: *Clostridium botulinium* neurotoxins, their structures and modes of action," in *Natural Toxicants in Foods. Progress and Prospects*, Watson, D.H., eds., Ellis Horwood Ltd., Chichester, England, pp. 11-43 (1986).

Shone, C.C., et al., "A 50-kDa fragment from the $NH_2$-terminus of the heavy subunit of *Clostridium botulinum* type A neurotoxin forms channels in lipid vesicles," *Eur. J. Biochem.* 167:175-180, Springer International (1987).

Shone, C.C., and Tranter, H.S., "Growth of Clostridia and Preparation of Their Neurotoxins," in *Clostridial Neurotoxins. The Molecular Pathogenesis of Tetanus and Botulism*, Montecucco, C., eds., Springer, Berlin, Germany, pp. 143-160 (1995).

Smith, M.C., et al., "Chelating Peptide-immobilized Metal Ion Affinity Chromatography," *J. Biol. Chem.* 263:7211-7215, American Society for Biochemistry (1988).

Studier, F.W., and Moffatt, B.A., "Use of Bacteriophage T7 RNA Polymerase to Direct Selective High-Level Expression of Cloned Genes," *J. Mol. Biol.* 189:113-130, Academic Press (1986).

Wilde, G.J., et al., "Attenuation and augmentation of ischaemia-related neuronal death by tumour necrosis factor-alpha in vitro," *Eur. J. Neurosci.* 12:3863-3870, Blackwell Science (2000).

Wilde, G.J., et al., "Differential vulnerability of the CA1 and CA3 subfields of the hippocampus to superoxide and hydroxyl radicals in vitro," *J. Neurochem.* 69:883-886, Blackwell Science (1997).

Yokosawa, N., et al., "Binding of botulinum type C1, D and E neurotoxins to neuronal cell lines and synaptosomes," *Toxicon* 29:261-264, Pergamon Press (1991).

Yokosawa, N., et al., "Binding of *Clostridium botulinum* type C neurotoxin to different neuroblastoma cell lines," *Infect. Immun.* 57:272-277, American Society For Microbiology (1989).

Bridgen et al., "Superoxide Dismutase from *Bacillus stearothermophilus*: Crystallization and Preliminary X-ray Diffraction Studies," *J. Mol. Biol.* 105:333-335, Academic Press (1976).

Fujii et al., "A Defect in the Mitochondrial Import of Mutant Mn-Superoxide Dismutase Produced in Sf21 Cells," *J. Biochem.* 124:340-346, The Japanese Biochemical Society (1998).

\* cited by examiner

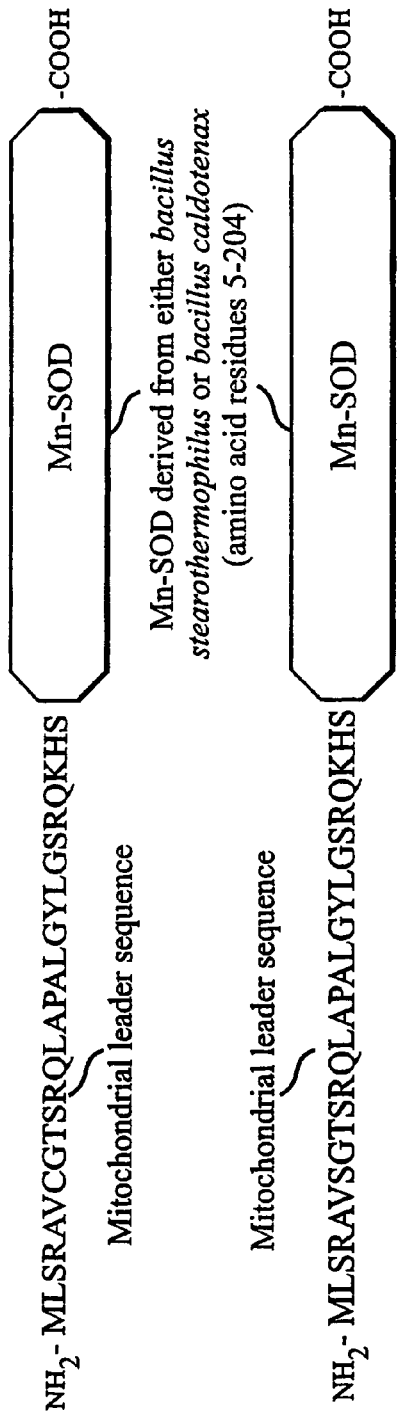
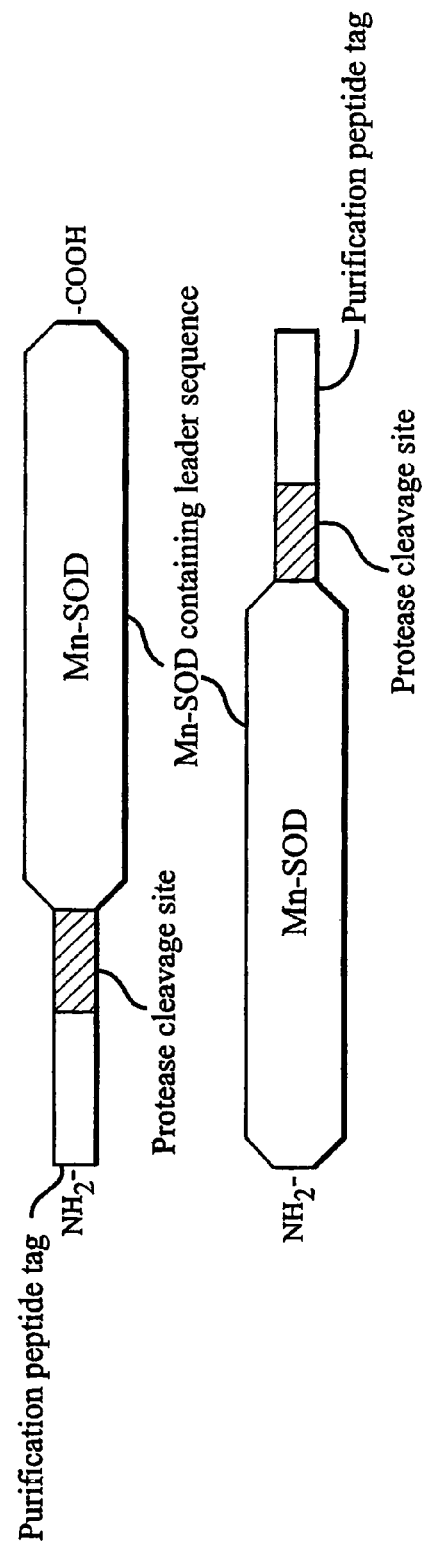

FIG. 4

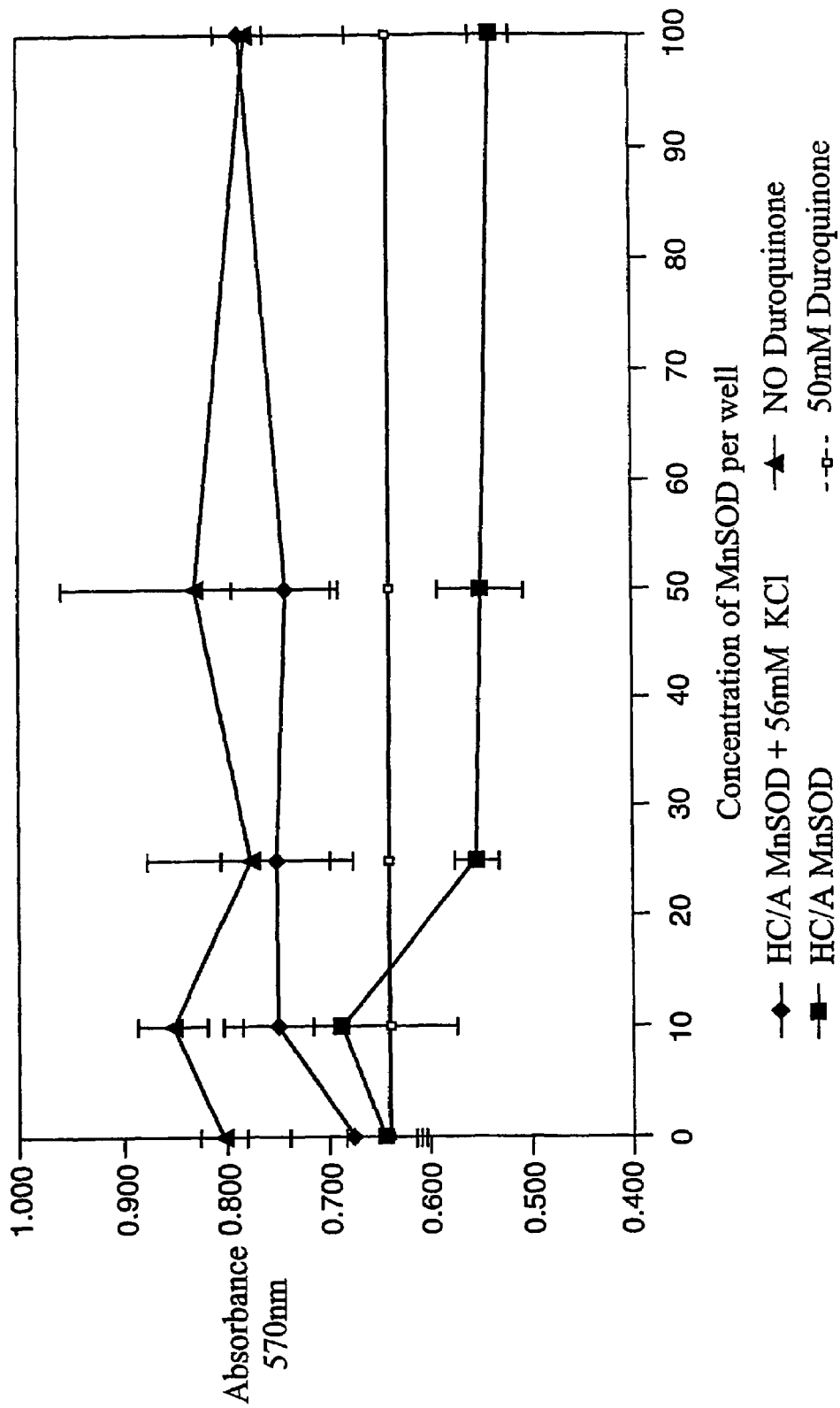

DELIVERY OF SUPEROXIDE DISMUTASE TO NEURONAL CELLS

The present invention relates to compositions and methods for delivery of superoxide dismutase (SOD) to neuronal cells, and in particular for delivery of SOD to mitochondria in those cells. The present invention also provides methods of making the constructs.

A number of nervous system disorders would benefit considerably from rapid intervention with several therapeutic agents. Examples of such disorders are global, focal or spinal cord ischaemia induced by stroke or injury. Neurones injured by trauma or ischaemia produce elevated levels of transmitter substances which result in high levels of reactive oxygen species. These reactive oxygen species, in high concentrations are toxic to both the neurones and the surrounding cells which potentiates and amplifies the damage process. Rapid therapeutic intervention with agents to reduce oxidative stress in cases of neuronal injury caused by stroke or trauma could therefore significantly limit this secondary damage process. One such potential therapeutic agent is superoxide dismutase which neutralises the harmful effects of the superoxide radicals by converting them to hydrogen peroxide and oxygen.

Francis and co-workers demonstrated that post-ischaemic infusion of Copper/Zinc superoxide dismutase (Cu/Zn-SOD) reduces cerebral infarction following ischaemia/reperfusion in rats (Experimental Neurology (1997) 146, 435-443) through the reduction of damaging free-radical oxygen. Lim et al. have shown than administration of Cu/Zn-SOD attenuates the level of reperfusion injury following spinal cord ischaemia in dogs (Ann. Thorac. Surg. (1986) 42, 282-286). Cuevas et al. have similarly demonstrated protective effects of SOD, both on neurological recovery and spinal infarction, in ischaemic reperfusion injury of the rabbit spinal cord (Acta Anat. (1990) 137, 303-310. A major problem in the use of such therapies is the maintenance of useful concentration of the active agent at the site of trauma. Enzymes such as Cu/Zn-SOD are rapidly cleared from the systemic circulation; in the case of the latter enzyme the $t_{1/2}$ in rat is 4-8 minutes. A number of strategies have been employed to overcome these difficulties. Matsumiaya et al. (Stroke (1991) 22, 1193-1200) conjugated Cu/Zn-SOD to polyethylene glycol to increase it half-life in the blood. Francis and co-workers (Experimental Neurology (1997) 146, 435-443) describe the neuronal delivery of Cn/Zn-SOD by fusion of the enzyme to the binding domain of tetanus toxin. None of these strategies, however, are particularly efficient at delivering the enzyme to the intracellular neuronal compartments where the enzyme can be effective.

In most eukaryotic species, two intracellular forms of superoxide dismutase exist: the Cu/Zn-SOD which is located within the cytoplasmic and nuclear compartments and manganese superoxide dismutase (Mn-SOD) which is located within the mitochondrial matrix. Human Mn-SOD is a tetrameric enzyme and is larger than the dimeric Cu/Zn-SOD. Several studies have shown that decreased Mn-SOD may be associated with one or more chronic diseases such as ovarian cancer (Nishida et al., (1995) Oncology Reports, 2,643-646) and diabetes (L'Abbe et al., (1994) Proc Soc Exp Biol Med, 207, 206-274). In addition, mice in which the Mn-SOD gene has been knocked out exhibit several novel pathogenic phenotypes including severe anaemia, degeneration of neurones in the basal ganglia and brainstem, and progressive motor disturbances characterised by weakness and rapid fatigue (Lebovitz et al., (1996) Proc Natl Acad Sci USA, 93, 9782-9787). In addition these mice showed extensive damage to the neuronal mitochondria. Overexpression of Mn-SOD in cell lines and transgenic mice showed that damage and apoptosis of neurones under oxidative stress was markedly reduced (Keller et al., (1998) Journal of Neuroscience, 18, 687-697). Mitochondrial damage was also reduced. These data showed that superoxide accumulation and subsequent mitochondrial damage play key roles in neuronal death induced by trauma both in vitro and in vivo. Delivery of agents which reduce the level of oxidative stress to neuronal cells may therefore reduce neuronal cell death and afford considerable therapeutic benefits.

Mn-SODs of bacterial origin such as that from *Bacillus stearothermophilus* or *B. caldotenax* consist of two subunits and are smaller than the human isoform which is a tetramer. *B. stearothermophilus* and *B. caldotenax* Mn-SOD also have considerably lower immunogenicity than the human isoform which is an advantage for continued therapeutic use. As enzymes for therapeutic applications, however, they suffer from similar drawbacks to other SODs in that very little of the administered enzyme is retained within the tissues where it would be therapeutically beneficial.

The botulinum neurotoxins are a family of seven structurally similar, yet antigenically different, protein toxins whose primary site of action is the neuromuscular junction where they block the release of the transmitter acetylcholine. The action of these toxins on the peripheral nervous system of man and animals results in the syndrome botulism, which is characterised by widespread flaccid muscular paralysis (Shone (1986) in 'Natural Toxicants in Foods', Editor D. Watson, Ellis Harwood, UK). Each of the botulinum neurotoxins consist of two disulphide-linked subunits; a 100 kDa heavy subunit which plays a role in the initial binding and internalisation of the neurotoxin into the nerve ending (Dolly et. al. (1984) Nature, 307, 457-460) and a 50 kDa light subunit which acts intracellularly to block the exocytosis process (McInnes and Dolly (1990) Febs Lett., 261, 323-326; de Paiva and Dolly (1990) Febs Lett., 277, 171-174). Thus it is the heavy chains of the botulinum neurotoxins that impart their remarkable neuronal specificity.

Tetanus toxin is structurally very similar to botulinum neurotoxins but its primary site of action is the central nervous system where it blocks the release of inhibitory neurotransmitters from central synapses (Renshaw cells). As described for the botulinum toxins above, it is domains within the heavy chain of tetanus toxin that bind to receptors on neuronal cells.

The binding and internalisation (translocation) functions of the clostridial neurotoxin (tetanus and botulinum) heavy chains can be assigned to at least two domains within their structures. The initial binding step is energy-independent and appears to be mediated by one or more domains within the $H_C$ fragment of the neurotoxin (C-terminal fragment of approximately 50 kDa) (Shone et al. (1985), Eur. J. Biochem., 151, 75-82) while the translocation step is energy-dependent and appears to be mediated by one or more domains within the $H_N$ fragment of the neurotoxin (N-terminal fragment of approximately 50 kDa).

Isolated heavy chains are non-toxic compared to the native neurotoxins and yet retain the high affinity binding for neuronal cells. Tetanus and the botulinum neurotoxins from most of the seven serotypes, together with their derived heavy chains, have been shown to bind a wide variety of neuronal cell types with high affinities in the nM range (e.g botulinum type B neurotoxin; Evans et al. (1986) Eur. J. Biochem. 154, 409-416).

Another key characteristic of the binding of these neurotoxins is that tetanus, botulinum A, B, $C_1$, D, E and F neurotoxins all appear to recognise distinct receptor populations, and collectively the clostridial neurotoxin heavy chains provide high affinity binding ligands that recognise a whole family of receptors that are specific to neuronal cells.

However, whilst it is known to provide a fusion of a SOD with a neurotoxin heavy chain, this fusion has been found to be ineffective for delivery of SOD to neuronal cells and inactive in in vitro assays for potential therapeutic activity.

It is an object of the invention to provide compositions and methods for delivery of SOD to neuronal cells. A further object is to provide compositions and methods for treatment or at least amelioration of conditions such as ischemic stroke.

Accordingly, the present invention provides a construct for delivering superoxide dismutase (SOD) to neuronal cells. In one aspect of the invention the construct consists of a SOD which has been combined with various functional protein domains to effect efficient targeting to the mitochondria within neuronal cells. The construct of specific embodiments of the invention, described in further detail below, contains the following elements:

- a SOD which contains a leader sequence for targeting SOD to the mitochondria;
- a dimeric SOD which has low immunogenicity and high stability;
- a SOD which is linked to a domain that effects translocation across lipid membranes;
- a linkage between the SOD and the translocation domain that is cleaved within the neuronal cytosol; and
- a domain which selectively targets the construct to neuronal cells.

A first aspect of the invention thus provides a composition for delivery of superoxide dismutase (SOD) to neuronal cells, comprising:

SOD; linked by a cleavable linker to a neuronal cell targeting component, comprising a first domain that binds to a neuronal cell and a second domain that translocates the SOD of the composition into the neuronal cell.

The linker is cleavable and thus, in use, after translocation of the SOD into the cell, the linker is cleaved to release SOD from the neuronal cell targeting domain. A suitable linker is a disulphide bridge between cysteine residues, one residue on the SOD and one residue on the neuronal cell targeting component, for example on the second domain. Another example of a linker is a site for a protease found in neuronal cells. In this way, the linker is such that it is cleaved within the cell, separating the SOD from the other translocated portions of the composition.

By SOD is meant a sequence that has superoxide dismutase activity, and may also comprise a further sequence or sequences conferring additional properties on that portion of the constructs. For example, the SOD optionally also includes a sequence targeting the SOD to mitochondria in a neuronal cell.

The SOD may be a hybrid of Mn-SOD and a sequence targeting the hybrid to mitochondria. The SOD may be of bacterial or human origin, or a derivative thereof, and may be comprised of sequences from more than one origin, provided that it has superoxide dismutase activity.

The first domain may suitably be selected from (a) neuronal cell binding domains of clostridial toxins; and (b) fragments, variants and derivatives of the domains in (a) that substantially retain the neuronal cell binding activity of the domains of (a). The second domain is suitably selected from (a) domains of clostridial neurotoxins that translocate polypeptide sequences into cells, and (b) fragments, variants and derivatives of the domains of (a) that substantially retain the translocating activity of the domains of (a).

In an embodiment of the invention a construct comprises SOD linked by a disulphide bridge to a neuronal cell targeting component comprising a first domain that binds to a neuronal cell and a second domain that translocates the SOD into the neuronal cell. This construct is made recombinantly as a single polypeptide having a cysteine residue on the SOD which forms a disulphide bridge with a cysteine residue on the second domain. The SOD is covalently linked, initially, to the second domain. Following expression of this single polypeptide SOD is cleaved from the second domain leaving the SOD linked only by the disulphide bridge to the rest of the construct.

A second aspect of the invention provides a pharmaceutical composition for treatment of oxidative damage to neuronal cells comprising a composition according to the invention with a pharmaceutically acceptable carrier. This composition may be used to deliver SOD to a neuronal cell, for example by administration of the composition by injection.

A third aspect of the invention provides a method of preparing a composition according to the invention, comprising chemically linking SOD, linker and neuronal cell targeting components. The SOD preferably is free of cysteine residues and the method preferably comprises treating the SOD with a cross-linker which will form a disulphide bridge with a cysteine residue on the neuronal cell targeting domain.

In a further embodiment of the third aspect of the invention, there is provided a method of making a composition according to the invention comprising expressing a DNA that codes for a polypeptide having SOD, a linker, a neuronal cell targeting component. The polypeptide may further comprise a purification sequence and the method may further comprise purifying the polypeptide using this sequence and then cleaving the polypeptide to remove the purification sequence to leave SOD, the linker and the neuronal cell targeting component.

By virtue of the combination of properties defined above, constructs of the invention are surprisingly efficient at transporting SOD to the mitochondria within neuronal cells. The ability of the superoxide dismutase to be translocated into the cytosol by virtue of the 'translocation domain' within the construct and the cleavage of the enzyme from the latter domain within the cell is key to this targeting efficiency. As such the construct of the invention has considerable therapeutic value in treating neuronal diseases which results from oxidative stress and has several advantages over previously described SOD formulations. Mitochondria within cells containing high levels of superoxide radicals are particularly sensitive to damage and the ability of the construct of the invention to target the SOD to these organelles offers considerable advantage in that the enzyme can act to remove the superoxide radicals where it is most required.

The construct of the invention may be used clinically in a variety of neuronal diseases which are caused or augmented by oxidative stress. Such conditions include ischaemic stoke, Parkinson's disease, Huntington's disease and motor neurone diseases. In the case of ischaemia/reperfusion injury caused by stroke or trauma, delivery of the construct of the invention to neurones of the hippocampus may afford considerable therapeutic benefits by reducing neuronal damage and death. Other neuronal diseases where the underlying cause is oxidative stress would also benefit from the therapeutic effects of the construct of the invention.

In a preferred aspect of the invention, the SOD is a dimeric, manganese superoxide dismutase (Mn-SOD) which is of bacterial origin and has low immunogenicity and high stability.

The use of a bacterial Mn-SOD in constructs has a number of advantages compared to the use of the human Mn-SOD isoform:

the low immunogenicity of the bacterial Mn-SOD is advantageous where repeated administration of the construct is required, in which cases the induction of adverse host immune responses is reduced; and the smaller size of constructs based on the dimeric bacterial Mn-SOD compared to human Mn-SOD (which is a tetramer) both reduces the likelihood of adverse immune responses and increases the rate of diffusion of the construct to its target tissue.

In exercise of an example of the invention, a bacterial Mn-SOD of low immunogenicity is derived from either *B. stearothermophilus* (sequence as reported by Brock and Walker (1980) Biochemistry, 19, 2873-2882) or *B. caldotenax* (gene and amino acid sequence as defined by Chambers et al., (1992) FEMS Microbiology Letters, 91, 277-284) to which a mitochondrial leader sequence has been fused to the N-terminus of the protein by recombinant technology. This Mn-SOD-leader hybrid is linked by a disulphide bridge to a translocation domain derived from a bacterial protein toxin, such as botulinum neurotoxin. The translocation domain, in turn is fused to a receptor binding domain derived from a clostridial neurotoxin (botulinum or tetanus). The construct is produced initially as a single polypeptide by recombinant technology and subsequently converted to the construct of the invention by selective cleavage with a proteolytic enzyme. To produce the construct of the invention, a loop motif containing a unique protease site (e.g amino acid sequences specifically cleaved by proteases such as factor Xa, enterokinase, thrombin) and a cysteine residue is introduced between the C-terminus of the Mn-SOD and the N-terminus of the translocation domain such that a disulphide bridge is formed between the Mn-SOD and the translocation domain. Subsequent cleavage of the protease site generates the active construct. The final construct, when analyzed by sodium dodecyl sulphate polyacrylamide gel electrophoresis in the presence of a reducing agent (e.g. dithiothreitol), dissociates into two major bands, one corresponding to the superoxide dismutase enzyme and a second corresponding to a polypeptide which contains the neuronal binding and translocation domains. In the absence of a reducing agent this dissociation does not occur and the complex is observed as a single major band on the gels.

Modification of Mn-SOD from *B. stearothermophilus* by addition of a mitochondrial targeting sequence offers several advantages over the use of human Mn-SOD which contains its own mitochondrial leader sequence. Firstly, the *B. stearothermophilus* Mn-SOD has a high thermal stability and low immunogenicity which allows administration of several doses of the enzyme without provoking an immune response from the host that would reduces its efficacy. Secondly, the *B. stearothermophilus* Mn-SOD is a small dimeric enzyme unlike the human Mn-SOD which is a tetramer. Recombinant constructs containing the latter enzyme would therefore have to be considerably larger and more complex in their structure.

In an embodiment of the invention, a DNA encoding a construct of the invention is made up by fusion of following DNA fragments commencing at the 5'end of the gene:

an oligonucleotide encoding a modified human mitochondrial leader sequence (amino acid sequence: MLSRAVCGTSRQLAPALGYLGSRQ (SEQ ID NO:10) or MLSRAVSGTSRQLAPALGYLGSRQ (SEQ ID NO:11);

an oligonucleotide encoding Mn-SOD from *B. stearothermophilus* (coding for the amino acid sequence as defined in Brock and Walker (1980) Biochemistry, 19, 2873-2882);

an oligonucleotide, encoding a linker peptide which contains the thrombin protease cleavage site and a cysteine residue for disulphide bridge formation (peptide sequence: CGLVPAGSGP);

an oligonucleotide encoding a translocation domain derived from a botulinum neurotoxin, (e.g. a DNA fragment coding for amino acid residues 449-871 of botulinum type A neurotoxin, or a DNA fragment coding for amino acid residues 441-858 of botulinum type B neurotoxin, or a DNA fragment coding for amino acid residues 440-864 of botulinum type F neurotoxin); and an oligonucleotide encoding the receptor binding domain of a botulinum neurotoxin or tetanus neurotoxin (e.g. a DNA fragment coding for amino acid residues 872-1296 of botulinum type A neurotoxin, or a DNA fragment coding for amino acid residues 859-1291 of botulinum type B neurotoxin, or a DNA fragment coding for amino acid residues 865-1278 of botulinum type F neurotoxin, or a DNA fragment coding for amino acid residues 880-1315 of tetanus neurotoxin).

The above DNA fragments may be obtained and constructed by standard recombinant DNA methods. Expression and purification of the assembled construct may be obtained with a variety of suitable expression hosts, e.g. *Escherichia coli, Bacillus subtilis*.

The translocation domain and neuronal binding domain of the construct may also be derived from combination of different clostridial neurotoxins. For example, the construct of the invention may contain a translocation domain derived from botulinum type F neurotoxin and a binding domain derived from botulinum type A neurotoxin.

A construct of the invention may be produced using protein chemistry techniques. Mn-SOD derived from *B. stearothermophilus* to which a mitoch ondrial leader sequence has been fused to the N-terminus of the protein by recombinant technology is modified with a heterobifunctional cross-linking reagent such as N-succinimidyl 3-[2-pyridyldithio] propionate (SPDP). The chemically modified enzyme is then combined to a cell targetting domain which contains the binding and translocation functional domains. The latter may be produced by recombinant technology or purified from the neurotoxins of *Clostridium botulinum* or *Clostridium tetani* by established methods. Chemical coupling of the SPDP-treated Mn-SOD may be accomplished using a free cysteine residue on the polypeptide containing the binding and translocation domains to give a construct of the invention.

Constructs of the invention may be introduced into either neuronal or non-neuronal tissue using methods known in the art. By subsequent specific binding to neuronal cell tissue, the targeted construct will exert its therapeutic effects. Alternatively, the construct may be injected near a site requiring therapeutic intervention, e.g. intrathecal or intracranial injection close to a site of trauma or disease.

The construct of the invention may also be administered with other agents which enhance its delivery to its target tissue. An example of such an agent is one which assists the passage of the construct of the invention through the blood-brain barrier to the central nervous system. The construct of the invention may also be administered in formulations with other therapeutic agents or drugs.

The dosage required for the construct of the invention will depend upon the application and could vary between 1 µg/kg to 100 mg/kg of body weight. The construct of the invention may be produced as a suspension, emulsion, solution or as a freeze dried powder depending on the application and properties of the release vehicle and its therapeutic contents. The construct of the invention may be resuspended or diluted in a variety of pharmaceutically acceptable liquids depending on the application.

"Clostridial neurotoxin" means a neurotoxin corresponding to tetanus neurotoxin or one of the seven botulinum neurotoxin serotypes (type A, B, $C_1$, D, E, F or G).

"Bind" in relation to the clostridial binding fragments, means the interaction between the clostridial fragment and one or more cell surface receptors or markers which results in localisation of the binding fragment or construct in the vicinity of the cell.

"Binding domain" of botulinum or tetanus neurotoxins means a domain of the toxin which retains the property of being able to bind the receptors on neuronal cells in a similar manner to the intact neurotoxin and encompasses native domains and fragments, variants and derivatives that retain this binding function. This property of the binding domain can be assessed in competitive binding assays. In such assays, radiolabelled neurotoxin (e.g botulinum type A neurotoxin) is contacted with neuronal cells in the presence of various concentrations of non-radiolabelled fragment representing the 'binding domain' of the neurotoxin. The ligand mixture is incubated with the cells, at low temperature (0-3° C.) to prevent ligand internalisation, during which competition between the radiolabelled neurotoxin and non-labelled 'binding domain' fragment may occur. In such assays when the unlabelled ligand used is binding domain of botulinum type A neurotoxin (residues 872-1296), the radiolabelled botulinum type A neurotoxin will be displaced from the neuronal cell receptors as the concentration of its non-labelled 'binding domain' is increased. The competition curve obtained in this case will therefore be representative of the behaviour of a 'binding domain' fragment being a able to bind the receptors on neuronal cells in a similar manner to the intact neurotoxin. This property of the binding domain may be used to identify other suitable protein domains which have the desired binding properties. Examples of binding domains derived from clostridial neurotoxins are as follows:

Botulinum type A neurotoxin—amino acid residues (872-1296)
Botulinum type B neurotoxin—amino acid residues (859-1291)
Botulinum type C neurotoxin—amino acid residues (867-1291)
Botulinum type D neurotoxin—amino acid residues (863-1276)
Botulinum type E neurotoxin—amino acid residues (846-1252)
Botulinum type F neurotoxin—amino acid residues (865-1278)
Botulinum type G neurotoxin—amino acid residues (864-1297)
Tetanus neurotoxin—amino acid residues (880-1315)

"Translocation domain" means a domain or fragment of a protein which effects transport of itself and/or other proteins and substances across a membrane or lipid bilayer and encompasses native domains and fragments, variants and derivatives that retain this binding function. The latter membrane may be that of an endosome where translocation will occur during the process of receptor-mediated endocytosis. Translocation domains can frequently be identified by the property of being able to form measurable pores in lipid membranes at low pH (Shone et al. (1987) Eur J. Biochem. 167, 175-180). The latter property of translocation domains may thus be used to identify other protein domains which could function as the translocation domain within the construct of the invention. Examples of translocation domains derived from bacterial neurotoxins are as follows:

Botulinum type A neurotoxin—amino acid residues (449-871)
Botulinum type B neurotoxin—amino acid residues (441-858)
Botulinum type C neurotoxin—amino acid residues (442-866)
Botulinum type D neurotoxin—amino acid residues (446-862)
Botulinum type E neurotoxin—amino acid residues (423-845)
Botulinum type F neurotoxin—amino acid residues (440-864)
Botulinum type G neurotoxin—amino acid residues (442-863)
Tetanus neurotoxin—amino acid residues (458-879)

"Translocation" in relation to translocation domain, means the internalisation events which occur after modified clostridial binding fragments bind to the cell surface. These events lead to the transport of substances into the cytosol of neuronal cells.

"Unique protease site" means a protease site incorporated into the construct such that the molecule may be proteolysed at pre-determined sites by a selected protease. The specificity of these proteases is such that cleavage to other parts of the construct does not occur. Examples of unique protease sites are the amino acid sequences cleaved by proteases such as: thrombin, factor Xa, enterokinase.

A fourth aspect of the invention provides a composition for delivery of a therapeutic agent to neuronal cells, comprising:
the therapeutic agent; linked by a cleavable linker to a neuronal cell targeting component, comprising a first domain that binds to a neuronal cell and a second domain that translocates the therapeutic agent of the composition into the neuronal cell.

Thus, in use, after translocation of the therapeutic agent into the cell, the linker is cleaved to release the therapeutic agent from the neuronal cell targeting domain. Other optional and preferred embodiments of the fourth aspect of the invention are as for the first-third aspects of the invention.

A fifth aspeect of the invention provides a polypeptide comprising a bacterial SOD, or derivative thereof, and a sequence for targeting the polypeptide to a mitochondria, such as a human mitochondria. The polypeptide may be chemically obtained by synthesis of otherwise or may be a fusion protein, obtained for example by expression of a nucleotide coding for the polypeptide.

The invention hence also provides, in a sixth aspect, a nucleotide encoding the polypeptide of the fifth aspect and in a seventh aspect a vector comprising the nucleotide of the sixth aspect. Also provided in an eigth aspect is a method of making a polypeptide according to the fifth aspect comprising expressing the nucleotide sequence of the sixth aspect. In a ninth aspect is provided a cell comprising the nucleotide sequence of the sixth aspect or the vector of the seventh.

There now follows description of specific embodiments of the invention illustrated by drawings in which:

FIG. 1 shows schematic examples of novel Mn-SODs derived from *B. stearothermophilus* and *B. caldotenax*. Two examples of mitochondrial leader sequences are shown. In one example, a cysteine residue at position 7 has been mutated to a serine residue. This change enables the production of the construct of the invention without the formation of disulphide bridges in undesirable positions;

FIG. 2 shows schematic examples of novel Mn-SOD fusion proteins showing the use of peptides and proteins to facilitate purification of the enzyme from the production strain. Various protein and peptide tags (such as histidine-6, S-peptide, maltose-binding protein, calmodulin-binding protein) may be fused to the Mn-SOD to allow rapid purification by affinity chromatography methods. Unique protease sites are incorporated between the purification tag and the Mn-SOD to enable removal of the tag after purification. Protein and peptide tags may be removed by treatment of the fusion protein with the relevant specific protease (e.g. factor Xa, thrombin, enterokinase);

FIG. 3 shows a recombinant Mn-SOD construct of the invention. From the N-terminus of the protein, the construct consists of the following components:—(1) a mitochondrial leader (targeting) sequence, (2) a Mn-superoxide dismutase, (3) a loop which contains a unique protease site and which allows disulphide bridge formation, (4) a translocation domain, (5) a neuronal targeting domain. The construct is produced as a single polypeptide; subsequent cleavage with a protease specific for the 'unique protease site' contained within the loop region generates the di-chain construct. Purification tags could added to the constructs as exemplified in FIG. 3;

Figure 4:
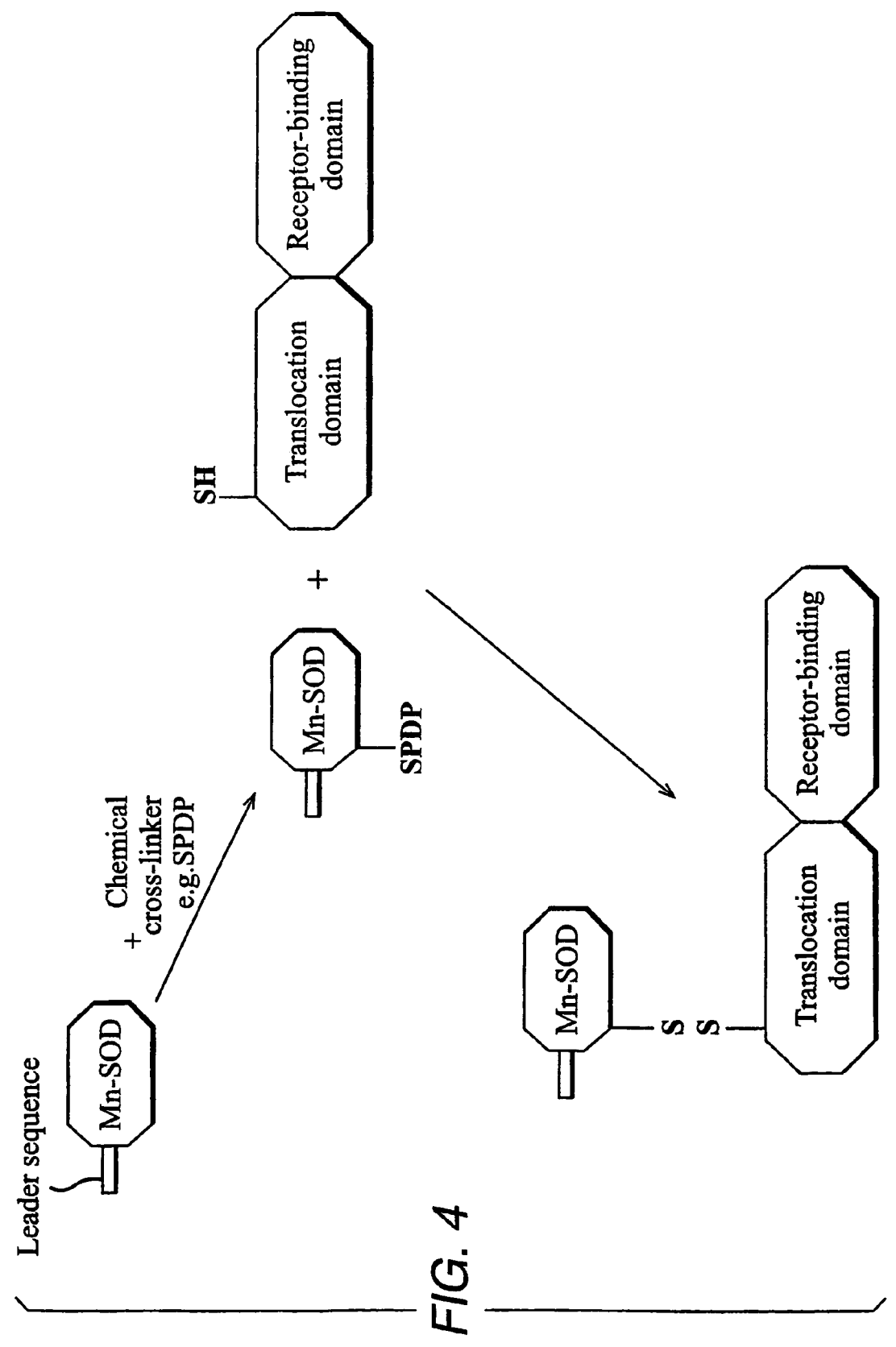

FIG. 4 shows the production of a Mn-SOD construct by chemical methods. The method uses a recombinant Mn-SOD, purified as described in Example 1 and coupled to a polypeptide containing the translocation and binding domains as described in Example 4; and FIG. 5 shows the results of an example to demonstrate the protective effects of a construct of the invention on NG108 cells subjected to oxidative stress by the addition of 50 μM duroquinone for four hours.

The application is also accompanied by a sequence listing in which:

SEQ ID NO: 1 shows the amino acid sequence of Mn-SOD from *B. caldotenax;*

SEQ ID NO: 2 shows the amino acid sequence of Mn-SOD from *B. stearothermophilus;*

SEQ ID NO: 3 shows the amino acid sequence of a construct of the invention comprising Mn-SOD from *B. stearothermophilus*, a linker that can be cleaved by thrombin, and a heavy chain derived from botulinum neurotoxin serotype A;

SEQ ID NO: 4 shows the amino acid sequence of a construct of the invention comprising Mn-SOD from *B. stearothermophilus*, a linker that can be cleaved by thrombin, and a heavy chain derived from botulinum neurotoxin serotype B;

SEQ ID NO: 5 shows the amino acid sequence of a construct of the invention comprising Mn-SOD from *B. stearothermophilus*, a linker that can be cleaved by thrombin, and a heavy chain derived from botulinum neurotoxin serotype F;

SEQ ID NO: 6 shows the amino acid sequence of a construct of the invention comprising a mitochondrial leader sequence from human Mn-SOD, Mn-SOD from *B. stearothermophilus*, a linker that can be cleaved by thrombin, and a heavy chain derived from botulinum neurotoxin serotype A;

SEQ ID NO: 7 shows the amino acid sequence of a construct of the invention comprising a mitochondrial leader sequence from human Mn-SOD, Mn-SOD from *B. stearothermophilus*, a linker that can be cleaved by thrombin, and a heavy chain derived from botulinum neurotoxin serotype B;

SEQ ID NO: 8 shows the amino acid sequence of a construct of the invention comprising a mitochondrial leader sequence from human Mn-SOD, Mn-SOD from *B. stearothermophilus*, a linker that can be cleaved by thrombin, and a heavy chain derived from botulinum neurotoxin serotype F; and SEQ ID NO: 9 shows the amino acid sequence for a polypeptide comprising a mitochondrial leader sequence from human Mn-SOD and Mn-SOD from *B. stearothermophilus;*

SEQ ID NO: 10 shows the amino acid sequence of a modified human mitochondrial leader sequence; and SEQ ID NO: 11 shows an amino acid sequence of a modified human mitochondrial leader sequence.

EXAMPLE 1

Production and Purification of Novel *B. stearothermophilus* Mn-SOD Containing a Mitochondrial Leader Sequence Standard molecular biology protocols were used for all genetic manipulations (eg. Sambrook et al. 1989, Molecular Cloning a Laboratory Manual, Second Edition, Cold Spring Harbor Laboratory Press, Cold Spring Harbor, N.Y.). A synthetic gene encoding the mitochondrial targeting sequence (amino acids 1-27) of the human Mn-SOD gene was cloned as an NdeI-Bam HI fragment into an expression vector so that the transcriptional start corresponds to the ATG codon within the NdeI site. The Mn-SOD gene from *B. stearothermophilus* or *B. caldotenax* was amplified using PCR to give a BglII site corresponding to the leucine amino acid at position 5 at the 5' end, and a BamHI site outside the stop codon at the 3' end. This BsIII-BamHI fragment was cloned into the expression vector carrying the mitochondrial targeting sequence (digested BamHI) to generate "in-frame" gene fusions. In addition to the wild type mitochondrial targeting sequence, a variant was constructed in which the cysteine at position 7 was changed to serine The recombinant Mn-SOD expressed in pET28a were produced with amino-terminal histidine (6 His) and T7 peptide tags allowing proteins to be purified by affinity chromatography on either a $Ni^{2+}$ charged column or an anti-T7 immunoaffinity column (Smith. et al. 1988, *Journal of Biological Chemistry*, 263: 7211-7215). Incorporation of a factor Xa protease cleavage between the peptide tag and the expressed Mn-SOD allowed this to be removed after purification. Briefly, cultures of *E. coli* BL21 (DE3) pET28a-Mn-SOD were grown in Terrific broth-kanamycin (30 μgml$^{-1}$) to an $OD_{600}$ nm of 2.0, and protein expression was induced by the addition of 500 μM IPTG for approximately 2 h. Cells were lysed by freeze/thaw followed by sonication, lysates cleared by centrifugation and supernatants loaded onto an anion exchange column (MonoQ™ column, on a Fast Protein Liquid Chromatography system; Pharmacia Biotech, Uppsala, Sweden). Eluted recombinant Mn-SOD was then desalted and further purified by affinity chromatography on a chelating sepharose column charged with $Ni^{2+}$ (Pharmacia Biotech, Uppsala, Sweden). After loading proteins onto the column and subsequent washing, the purified Mn-SOD was eluted with imidazole. All buffers used were as specified by the manufacturer.

A 'maltose binding protein' purification tag was also employed for the purification of some batches of Mn-SOD. The use of this system is described in detail in New England Biolabs Instruction Manual "Protein Fusion and Purification System" (ver 3.02).

Other tags and protease cleavage site may also be incorporated into the sequence to facilitate purification of Mn-SOD as exemplified in FIG. 2.

For purification of a novel *B. stearothermophilus* Mn-SOD which was not conjugated to protein purification tag, the following procedure was used. After harvesting, cells were broken by high pressure homogenisation crude extracts were clarified by centrifugation and batch purified on DE-23 cellulose. The fraction eluted with 0.4M NaCl contained the Mn-SOD. This fraction was then further purified by various chromatographic media using the following sequence:

DEAE-Sepharose ion exchange chromatography at pH 8.0; elution of the Mn-SOD with a NaCl gradient;
hydroxylapatite chromatography at pH 6.8; elution of Mn-SOD with a phosphate gradient at pH 6.8;
ion exchange chromatography on Q-Sepharose at pH 7.5; elution with a NaCl gradient; and
gel filtration on Sephacryl S-200.

The purified Mn-SOD may be dialysed against Hepes buffer (0.1M, pH 7.4) containing 0.15M NaCl and stored at −80° C.

EXAMPLE 2

Preparation and Purification of a Recombinant Mn-SOD Construct of the Invention

Standard molecular biology protocols were used for all genetic manipulations (eg. Sambrook et al. 1989, Molecular Cloning a Laboratory Manual, Second Edition, Cold Spring Harbor Laboratory Press, Cold Spring Harbor, N.Y.). Various DNA fragments of the construct were generated using Recursive PCR reactions (Prodromou & Pearl 1992, *Protein Engineering*, 5: 827-829) using self-priming oligonucleotides containing the desired sequence. For the expression of clostridial neurotoxin fragments the codon bias and GC/AT base ratio was adjusted for ease of expression in *E. coli*. Fragments were cloned sequentially into pLitmus 38 (New England Biolabs, Inc., Beverly, Mass.) to assemble the entire gene. Constructs for expression were sub-cloned into pET28b (Novagen Inc., Madison, Wis.) replacing the EcoR1-HindIII fragment. The ligation reactions were transformed into *E. coli* DH5α (Life Technologies Inc., Gaithersburg, Md.). Plasmid DNA was amplified, purified and screened for the presence of the appropriate sequence (Ausubel et al. 1989, Current Protocols in Molecular Biology, John Wiley & Sons, New York). Gene constructions confirmed as possessing the correct sequences were then transformed into the expression host *E. coli* BL21 (DE3) (Studier & Moffatt 1986, *Journal of Molecular Biology*, 189: 113-130).

The recombinant constructs expressed in pET28 were produced with amino-terminal histidine (6 His) and T7 peptide tags allowing proteins to be purified by affinity chromatography on either a $Ni^{2+}$ charged column or an anti-T7 immunoaffinity column (Smith et al. 1988, *Journal of Biological Chemistry*, 263:7211-7215). Incorporation of a factor X protease cleavage between the peptide tags and the expressed Mn-SOD Constructs allowed these to be removed after purification. Briefly, cultures of *E. coli* BL21 (DE3) pET28-Mn-SOD Construct were grown in Terrific broth-kanamycin (30 µgml$^{-1}$) to an $OD_{600}$ nm of 2.0, and protein expression was induced by the addition of 500 µM IPTG for approximately 2 h. Cells were lysed by freeze/thaw followed by sonication, lysates cleared by centrifugation and supernatants loaded onto an anion exchange column (MonoQ™ column on a Fast Protein Liquid Chromatography system; Pharmacia Biotech, Uppsala, Sweden). Eluted recombinant Mn-SOD Construct was then desalted and further purified by affinity chromatography on a chelating sepharose column charged with $Ni^{2+}$ (Pharmacia Biotech, Uppsala, Sweden). After loading proteins onto the column and subsequent washing, the purified Construct was eluted with imidazole. All buffers used were as specified by the manufacturer.

A 'maltose binding protein' purification tag was also employed for the purification some batches of Mn-SOD Constructs. The use of this system is described in detail in New England Biolabs Instruction Manual "Protein Fusion and Purification System" (ver 3.02).

It would also be evident to anyone skilled in the art that other tags and protease cleavage site may also be incorporated into the sequence to facilitate purification as exemplified in FIG. 3.

The amino sequences of several recombinant Mn-SOD constructs are shown in the sequence listing.

EXAMPLE 3

Preparation of Botulinum Heavy Chains by Chemical Methods

The various serotypes of the clostridial neurotoxins may be prepared and purified from various toxigenic strains of *Clostridium botulinum* and *Clostridium tetani* by methods employing standard protein purification techniques as described previously (Shone and Tranter 1995, Current Topics in Microbiology, 194, 143-160; Springer). Samples of botulinum neurotoxin (1 mg/ml) are dialysed against a buffer containing 50 mM Tris-HCl pH 8.0, 1M NaCl and 2.5M urea for at least 4 hours at 4° C. and then made 100 mM with dithiothreitol and incubated for 16 h at 22° C. The cloudy solution which contains precipitated light chain is then centrifuged at 15000×g for 2 minutes and the supernatant fluid containing the heavy chain retained and dialysed against 50 mM Hepes pH 7.5 containing 0.2M NaCl and 5 mM dithiothreitol for at least 4 hours at 4° C. The dialysed heavy chain is centrifuged at 15000×g for 2 minutes and the supernatant retained and dialysed thoroughly against 50 mM Hepes pH 7.5 buffer containing 0.2M NaCl and stored at −70° C. The latter procedure yields heavy chain >95% pure with a free cysteine residue which can be used for chemical coupling purposes. Biological (binding) activity of the heavy chain may be assayed as described in Example 5.

The heavy chains of the botulinum neurotoxins may also be produced by chromatography on QAE Sephadex as described by the methods in Shone and Tranter (1995), (Current Topics in Microbiology, 194, 143-160; Springer).

EXAMPLE 4

Production of Mn-SOD Constructs by Chemical Methods

*B. stearothermophilus* Mn-SOD fused to a mitochondrial leader sequence was purified as described in Example 1. The Mn-SOD was chemically modified by treatment with a 3-5 molar excess of N-succinimidyl 3-[2-pyridyldithio]propionate (SPDP) in 0.05M Hepes buffer pH 7.0 containing 0.1M NaCl for 60 min at 22° C. The excess SPDP was removed by dialysis against the same buffer at 4° C. for 16 h. The substituted SOD was then mixed in a 1:2.5 molar ratio with heavy chain purified from *Clostridium botulinum* type A neurotoxin purified as described in Example 3 and incubated at 4° C. for 16 h. During the incubation period the Mn-SOD was conjugated to the botulinum heavy chain fragment by free sulphydryl groups (see FIG. 4). After incubation, the Mn-SOD-construct was purified by gel filtration chromatography on Sephadex G200.

Constructs of the invention may also be formed by the above method using polypeptides containing the translocation and binding domains that have been produced by recombinant technology as outlined in Example 2.

EXAMPLE 5

Assay of the Biological Activity of Constructs—Demonstration of High Affinity Binding to Neuronal Cells Clostridial neurotoxins may be labelled with 125-iodine using chloramine-T and its binding to various cells assessed by standard methods such as described in Evans et al. 1986, Eur J. Biochem., 154, 409 or Wadsworth et al. 1990, Biochem. J. 268, 123). In these experiments the ability of Mn-SOD constructs to compete with native clostridial neurotoxins for receptors present on neuronal cells or brain synaptosomes was assessed. All binding experiments were carried out in binding buffers. For the botulinum neurotoxins this buffer consisted of: 50 mM HEPES pH 7.0, 30 mM NaCl, 0.25% sucrose, 0.25% bovine serum albumin. For tetanus toxin, the binding buffer was: 0.05M tris-acetate pH 6.0 containing 0.6% bovine serum albumin. In a typical binding experiment the radiolabelled clostridial neurotoxin was held at a fixed concentration of between 1-20 nM. Reaction mixtures; were prepared by mixing the radiolabelled toxin with various concentrations of unlabelled neurotoxin or construct. The reaction mixture were then added to neuronal cells or rat brain synaptosomes and then incubated at 0-3° C. for 2 hr. After this period the neuronal cells of synaptosomes were washed twice with binding ice-cold binding buffer and the amount of labelled clostridial neurotoxin bound to cells or synaptosomes was assessed by γ-counting. In an experiment using an Mn-SOD construct which contained the binding domain from botulinum type A neurotoxin, the construct was found to compete with $^{125}$I-labelled botulinum type A neurotoxin for neuronal cell receptors in a similar manner to unlabelled native botulinum type A neurotoxin. These data showed that the construct had retained binding properties of the native neurotoxin.

EXAMPLE 6

Assay of the Biological Activity of Constructs—Measurement of the Mn-SOD Activity Mn-SOD activity in samples and constructs was measured by a modification (Brehm et al. (1991) Appl. Microbiol. Biotechnol., 36,358-363) of the procedure described by McCord and Fridovich (J. Biol. Chem. (1969), 244, 6049-6055). Aliquots (20 μl) of samples or constructs containing Mn-SOD were added to 1 ml of 0.05M potassium phosphate buffer pH 7.5 containing $1\times10^{-4}$ M EDTA, $2.5\times10^{-5}$ M ferricytochrome C and $7\times10^{-3}$ M sodium xanthine in a thermostatted cuvette at 30° C. Sufficient xanthine oxidase was added to produce a rate of reduction of the ferricytochrome C at 550 nm of approx. 0.1 absorbance units/minute in the absence of Mn-SOD. Under these conditions the amount Mn-SOD that was required to reduce the rate of reduction of ferricytochrome C by 50% was defined as one unit of activity.

Using such assays the Mn-SOD activity within constructs was assessed.

EXAMPLE 7

Demonstration of the Targeting of Mn-SOD to the Mitochondria of Neuronal Cells by Constructs of the Invention Mn-SOD construct containing the translocation and targeting domains derived from botulinum type A neurotoxin was incubated at various concentrations (0.01-10 μM final concentration) with a neuroblastoma cell line NG108. Incubations were carried out over a 6 h period or overnight at 37° C. In some experiments, construct radiolabelled with $^{125}$iodine was used. After incubation with the construct cells, were removed from culture flasks by gentle scraping and centrifuged at 200×g. Cells were then resuspended in breaking buffer (0.6M mannitol, 20 mM hepes pH 7.4 and 1 mM phenylmethylsulphonyl chloride) and homogenised in a Dounce homogeniser. The homogenate was centrifuged at 200×g for 5 min and then the supernatant fluid recovered and centrifuged at 8000×g for 10 min. The 200×g pellet (nuclear fraction) were pooled and resuspended in phosphate buffered saline. The 8000×g pellets (mitochondrial fraction) were also pooled and resuspended in phosphate buffered saline. The supernatant fluid was saved and used to represent the cytosolic fraction.

Analysis of the sub-cellular distribution of Mn-SOD was carried out by Western blot analysis and, where radiolabelled construct was used, by analysis of the $^{125}$I-labelled construct components by γ-counting and by autoradiography of cell fractions which had been separated by electrophoresis on SDS-polyacrylamide gels. For Western blot analysis, proteins in the cell fractions were separated by electrophoreses on SDS-polyacrylamide gels and then transferred to nitrocellulose membrane as described previously (Towbin et al. Proc. (1979) Natl. Acad. Sci. USA, 76, 4350). The presence of Mn-SOD in protein bands on nitrocellulose membranes was assessed by incubation with rabbit anti-Mn-SOD antibody followed by washing and incubation with anti-rabbit peroxidase conjugate. Addition of peroxidase substrates (3,3',5,5'-tetramethyl benzidine and $H_2O_2$) allowed visualisation and quantitation of the Mn-SOD in the various sub-cellular protein fractions. An enhanced chemiluminescence system (Amersham International) was also used in some experiments to increase the sensitivity.

EXAMPLE 8

Formulation of the Mn-SOD Construct for Clinical Use

In a formulation of the Mn-SOD construct for clinical use, recombinant Mn-SOD construct would be prepared under current Good Manufacturing Procedures. The construct would be transferred, by dialysis, to a solution to give the product stability during freeze-drying. Such a formulation may contain Mn-SOD construct (10 mg/ml) in 5 mM HEPES buffer (pH 7.2), 50 mM NaCl, 1% lactose. The solution, after sterile filtration, would be aliquotted, freeze-dried and stored under nitrogen at −20° C.

EXAMPLE 9

Use of an Mn-SOD Construct to Treat Stroke

In a typical case of a middle aged or elderly man diagnosed as suffering from stroke, treatment with an Mn-SOD construct would begin immediately, ideally within 6 hours of the stroke occurring. Doses of the Mn-SOD construct (e.g. 100 mg) reconstituted in a sterile saline solution would be administered intravenously. Further doses of the construct would be administered daily for 5-10days. Such a patient would be expected to display reduced levels of ischaemia/reperfusion damage as assessed by magnetic resonance imaging compared to a similarly affected patient receiving no treatment. Relative improvements to muscle strength and co-ordination (MRC motor score) would be expected to be observed over the subsequent 12 month period.

EXAMPLE 10

Method to Demonstrate Neuroprotection of Cells by MnSOD-Heavy Chain Conjugates Neuroblastoma cell line NG108-15 (*Nature* (1998) 336:p 185 were seeded at a density of $3\times10^4$ cells/ml in 96 well microtitre plates coated with poly-D-lysine. Plates were grown for 3 days at 37° C. in a $CO_2$ incubator (5% $CO_2$ 95% air). MnSOD or leader-MnSOD conjugates were prepared with purified heavy chain of botulinum neurotoxin serotype A (BoNT/A HC) as described. The concentration of SOD was estimated and the conjugate diluted to give the specified amount of conjugate in a total volume of 200 µl serum free medium. Conjugate was added to wells in the presence or absence of 56 mM KCl, 2 mM $CaCl_2$. The cells were incubated with conjugate for 1 hour. The conjugate was replaced with either serum free medium or serum free medium containing 50 µM duroquinone and incubated at 37° C. for 4 hours in the $CO_2$ incubator to induce oxidative stress. The media was removed after 4 hours and replaced with the dye 3-(4,5-Dimethylthiazol-2-yl)-2,5-diphenyltetrazolium bromide (MTT) at a final concentration of 0.25 mg/ml in serum free medium and incubated for 2 hours (according to the method of Mattson, M P, et al (1995) *Methods in Cell Biology* 46:187-216) The conversion of MTT to formazan dye crystals has been shown to be related to mitochondrial respiratory chain activity (Musser, D A, and Oseroff, A R (1994) *Journal of Immunology* 59:621-626). MTT was removed and crystals solubilised with dimethylsulfoxide (DMSO). Absorbance at 570 nm was measured using a Labsystems Multiskan Plus MkII spectrophotometer and the results shown in FIG. 5.

FIG. 5 shows that a construct of the invention was able to protect neuronal cells against the mitochondrial-focused oxidative stress produced by duroquinone.

EXAMPLE 11

Preparation and Purification of Recombinant MnSOD and Leader Sequence MnSOD

Standard molecular biology protocols were used for all genetic manipulations (Sambrook et al 1989, Molecular cloning; A laboratory manual. Second Edition, Cold Spring Harbor Laboratory Press, New York.). The MnSOD gene from either *B. stearothermophilus* or *B.caldotenax* was amplified by PCR to engineer a BamHI site (resulting in the replacement of nucleotides 1-15). A synthetic oligonucleotide corresponding to the mitochondrial leader sequence of human MnSOD (bases 1-81 of the human gene) was subcloned into the BamHI site to generate leader-MnSOD. PCR was used to add a Factor Xa cleavage site immediately adjacent to the methionine at the start of the leader sequence. Similarly a Factor Xa cleavage site was engineered immediately adjacent to the methionine at the start of the native MnSOD gene. Constructs were sequenced to confirm the presence of the correct sequence. Constructs for expression were subcloned into the expression vector pET28a (Novagen Inc, Madison, Wis.) as an EcoRI fragment and the orientation of the fragments checked. Clones with confirmed sequences were used to transform expression host *E.coli* BL21 (DE3) (Studier and Moffatt 1986 *Journal of Molecular Biology* 189:113-130). Examples 2 and 3 above provide detailed methods.

The recombinant proteins expressed from pET28a contain amino-terminal histidine (6-His) and T7 peptide tags allowing proteins to be purified by affinity chromatography on either a $Cu^{2+}$ charged metal chelate column or an anti-T7 immunoaffinity column. Incorporation of the Factor Xa site between the peptide tags and the start of either MnSOD or leader MnSOD allows the precise removal of the peptide tags after purification. Cultures of *E.coli* BL21 (DE3) pET28a-MnSOD or BL21 (DE3) pET28a-leader-MnSOD were grown in Terrific Broth containing 30 µg/ml kanamycin and 0.5% (w/v) glucose to an $OD_{600}$ of 2.0 and protein expression was induced with 500 µM IPTG for 2 hours. Cells were lysed by sonication, cell debris pelleted by centrifugation and the supernatant loaded onto a metal chelate column charged with $Cu^{2+}$ (Amersham-Pharmacia Biotech, Uppsala, Sweden). After loading proteins on the column and washing, proteins were eluted using imidazole. All buffers were used as specified by manufacturers. Factor Xa cleavage of the eluted protein was carried out according to manufacturers instructions.

The invention thus provides constructs and methods for delivery of SOD to neuronal cells.

The invention claimed is:

1. A conjugate for delivery of superoxide dismutase (SOD) to a mitochondrion in a neuronal cell, comprising:
   (i) SOD and a leader sequence, wherein said leader sequence targets the SOD to said mitochondrion; and
   (ii) a neuronal cell targeting component,
       wherein said neuronal cell targeting component is linked to the SOD by a cleavable linker selected from the group consisting of (a) a disulfide bridge, and (b) a site for a protease found in neuronal cells,
       and wherein said neuronal targeting component comprises a first domain that binds to a neuronal cell, wherein said first domain comprises a clostridial neurotoxin cell binding domain, and a clostridial neurotoxin translocation domain that translocates the SOD into said neuronal cell.

2. The conjugate of claim 1, wherein the first domain comprises a $H_C$ fragment of a clostridial neurotoxin H-chain.

3. The conjugate of claim 1, wherein the clostridial neurotoxin translocation domain comprises a $H_N$ fragment of a clostridial neurotoxin H-chain.

4. The conjugate of claim 1, wherein the SOD is Mn-SOD.

5. The conjugate of claim 1, wherein the leader sequence that targets the SOD to the mitochondrion is derived from human Mn-SOD.

* * * * *

SEQUENCE LISTING

<160> NUMBER OF SEQ ID NOS: 11

<210> SEQ ID NO 1
<211> LENGTH: 204
<212> TYPE: PRT
<213> ORGANISM: Bacillus caldotenax

<400> SEQUENCE: 1

Met Pro Phe Glu Leu Pro Ala Leu Pro Tyr Pro Tyr Asp Ala Leu Glu
1               5                   10                  15

Pro His Ile Asp Lys Glu Thr Met Asn Ile His His Thr Lys His His
            20                  25                  30

Asn Thr Tyr Val Thr Asn Leu Asn Ala Ala Leu Glu Gly His Pro Asp
        35                  40                  45

Leu Gln Asn Lys Ser Leu Glu Glu Leu Leu Ser Asn Leu Glu Ala Leu
    50                  55                  60

```
Pro Glu Ser Ile Arg Thr Ala Val Arg Asn Asn Gly Gly Gly His Ala
 65                  70                  75                  80

Asn His Ser Leu Phe Trp Thr Ile Leu Ser Pro Asn Gly Gly Gly Glu
                 85                  90                  95

Pro Thr Gly Glu Leu Ala Glu Ala Ile Asn Lys Lys Phe Gly Ser Phe
            100                 105                 110

Thr Ala Phe Lys Asp Glu Phe Ser Lys Ala Ala Ala Gly Arg Phe Gly
            115                 120                 125

Ser Gly Trp Ala Trp Leu Val Val Asn Asn Gly Glu Leu Glu Ile Thr
130                 135                 140

Ser Thr Pro Asn Gln Asp Ser Pro Ile Met Glu Gly Lys Thr Pro Ile
145                 150                 155                 160

Leu Gly Leu Asp Val Trp Glu His Ala Tyr Tyr Leu Lys Tyr Gln Asn
                165                 170                 175

Arg Arg Pro Glu Tyr Ile Ala Ala Phe Trp Asn Ile Val Asn Trp Asp
            180                 185                 190

Glu Val Ala Lys Arg Tyr Ser Glu Ala Lys Ala Lys
            195                 200
```

<210> SEQ ID NO 2
<211> LENGTH: 204
<212> TYPE: PRT
<213> ORGANISM: Bacillus stearothermophilus

<400> SEQUENCE: 2

```
Met Pro Phe Glu Leu Pro Ala Leu Pro Tyr Pro Tyr Asp Ala Leu Glu
  1               5                  10                  15

Pro His Ile Asp Lys Glu Thr Met Asn Ile His His Thr Lys His His
                 20                  25                  30

Asn Thr Tyr Val Thr Asn Leu Asn Ala Ala Leu Glu Gly His Pro Asp
             35                  40                  45

Leu Gln Asn Lys Ser Leu Glu Glu Leu Leu Ser Asn Leu Glu Ala Leu
         50                  55                  60

Pro Glu Ser Ile Arg Thr Ala Val Arg Asn Asn Gly Gly Gly His Ala
 65                  70                  75                  80

Asn His Ser Leu Phe Trp Thr Ile Leu Ser Pro Asn Gly Gly Gly Glu
                 85                  90                  95

Pro Thr Gly Glu Leu Ala Asp Ala Ile Asn Lys Lys Phe Gly Ser Phe
            100                 105                 110

Thr Ala Phe Lys Asp Glu Phe Ser Lys Ala Ala Ala Gly Arg Phe Gly
            115                 120                 125

Ser Gly Trp Ala Trp Leu Val Val Asn Asn Gly Glu Leu Glu Ile Thr
130                 135                 140

Ser Thr Pro Asn Gln Asp Ser Pro Ile Met Glu Gly Lys Thr Pro Ile
145                 150                 155                 160

Leu Gly Leu Asp Val Trp Glu His Ala Tyr Tyr Leu Lys Tyr Gln Asn
                165                 170                 175

Arg Arg Pro Glu Tyr Ile Ala Ala Phe Trp Asn Val Val Asn Trp Asp
            180                 185                 190

Glu Val Ala Lys Arg Tyr Ser Glu Ala Lys Ala Lys
            195                 200
```

<210> SEQ ID NO 3
<211> LENGTH: 1067
<212> TYPE: PRT
<213> ORGANISM: Artificial Sequence

```
<220> FEATURE:
<223> OTHER INFORMATION: Construct comprising Mn-SOD from B.
      stearothermophilus, a linker, and a heavy chain from botulinium
      neurotoxin serotype A

<400> SEQUENCE: 3

Met Pro Phe Glu Leu Pro Ala Leu Pro Tyr Pro Tyr Asp Ala Leu Glu
1               5                   10                  15

Pro His Ile Asp Lys Glu Thr Met Asn Ile His His Thr Lys His His
                20                  25                  30

Asn Thr Tyr Val Thr Asn Leu Asn Ala Ala Leu Glu Gly His Pro Asp
            35                  40                  45

Leu Gln Asn Lys Ser Leu Glu Glu Leu Leu Ser Asn Leu Glu Ala Leu
        50                  55                  60

Pro Glu Ser Ile Arg Thr Ala Val Arg Asn Asn Gly Gly Gly His Ala
65                  70                  75                  80

Asn His Ser Leu Phe Trp Thr Ile Leu Ser Pro Asn Gly Gly Gly Glu
                85                  90                  95

Pro Thr Gly Glu Leu Ala Asp Ala Ile Asn Lys Lys Phe Gly Ser Phe
                100                 105                 110

Thr Ala Phe Lys Asp Glu Phe Ser Lys Ala Ala Ala Gly Arg Phe Gly
            115                 120                 125

Ser Gly Trp Ala Trp Leu Val Val Asn Asn Gly Glu Leu Glu Ile Thr
        130                 135                 140

Ser Thr Pro Asn Gln Asp Ser Pro Ile Met Glu Gly Lys Thr Pro Ile
145                 150                 155                 160

Leu Gly Leu Asp Val Trp Glu His Ala Tyr Tyr Leu Lys Tyr Gln Asn
                165                 170                 175

Arg Arg Pro Glu Tyr Ile Ala Ala Phe Trp Asn Val Val Asn Trp Asp
                180                 185                 190

Glu Val Ala Lys Arg Tyr Ser Glu Ala Lys Ala Lys Gln Arg Ser Cys
            195                 200                 205

Gly Leu Val Pro Arg Gly Ser Gly Pro Gly Ser Ala Leu Asn Asp Leu
        210                 215                 220

Cys Ile Lys Val Asn Asn Trp Asp Leu Phe Phe Ser Pro Ser Glu Asp
225                 230                 235                 240

Asn Phe Thr Asn Asp Leu Asn Lys Gly Glu Glu Ile Thr Ser Asp Thr
                245                 250                 255

Asn Ile Glu Ala Ala Glu Glu Asn Ile Ser Leu Asp Leu Ile Gln Gln
                260                 265                 270

Tyr Tyr Leu Thr Phe Asn Phe Asp Asn Glu Pro Glu Asn Ile Ser Ile
            275                 280                 285

Glu Asn Leu Ser Ser Asp Ile Ile Gly Gln Leu Glu Leu Met Pro Asn
        290                 295                 300

Ile Glu Arg Phe Pro Asn Gly Lys Lys Tyr Glu Leu Asp Lys Tyr Thr
305                 310                 315                 320

Met Phe His Tyr Leu Arg Ala Gln Glu Phe Glu His Gly Lys Ser Arg
                325                 330                 335

Ile Ala Leu Thr Asn Ser Val Asn Glu Ala Leu Leu Asn Pro Ser Arg
            340                 345                 350

Val Tyr Thr Phe Phe Ser Ser Asp Tyr Val Lys Lys Val Asn Lys Ala
        355                 360                 365

Thr Glu Ala Ala Met Phe Leu Gly Trp Val Glu Gln Leu Val Tyr Asp
        370                 375                 380
```

-continued

```
Phe Thr Asp Glu Thr Ser Glu Val Ser Thr Thr Asp Lys Ile Ala Asp
385                 390                 395                 400

Ile Thr Ile Ile Ile Pro Tyr Ile Gly Pro Ala Leu Asn Ile Gly Asn
            405                 410                 415

Met Leu Tyr Lys Asp Asp Phe Val Gly Ala Leu Ile Phe Ser Gly Ala
            420                 425                 430

Val Ile Leu Leu Glu Phe Ile Pro Glu Ile Ala Ile Pro Val Leu Gly
            435                 440                 445

Thr Phe Ala Leu Val Ser Tyr Ile Ala Asn Lys Val Leu Thr Val Gln
        450                 455                 460

Thr Ile Asp Asn Ala Leu Ser Lys Arg Asn Glu Lys Trp Asp Glu Val
465                 470                 475                 480

Tyr Lys Tyr Ile Val Thr Asn Trp Leu Ala Lys Val Asn Thr Gln Ile
                485                 490                 495

Asp Leu Ile Arg Lys Lys Met Lys Glu Ala Leu Glu Asn Gln Ala Glu
                500                 505                 510

Ala Thr Lys Ala Ile Ile Asn Tyr Gln Tyr Asn Gln Tyr Thr Glu Glu
            515                 520                 525

Glu Lys Asn Asn Ile Asn Phe Asn Ile Asp Asp Leu Ser Ser Lys Leu
            530                 535                 540

Asn Glu Ser Ile Asn Lys Ala Met Ile Asn Ile Asn Lys Phe Leu Asn
545                 550                 555                 560

Gln Cys Ser Val Ser Tyr Leu Met Asn Ser Met Ile Pro Tyr Gly Val
                565                 570                 575

Lys Arg Leu Glu Asp Phe Asp Ala Ser Leu Lys Asp Ala Leu Leu Lys
                580                 585                 590

Tyr Ile Tyr Asp Asn Arg Gly Thr Leu Ile Gly Gln Val Asp Arg Leu
            595                 600                 605

Lys Asp Lys Val Asn Asn Thr Leu Ser Thr Asp Ile Pro Phe Gln Leu
            610                 615                 620

Ser Lys Tyr Val Asp Asn Gln Arg Leu Leu Ser Thr Phe Thr Glu Tyr
625                 630                 635                 640

Ile Lys Asn Ile Ile Asn Thr Ser Ile Leu Asn Leu Arg Tyr Glu Ser
                645                 650                 655

Asn His Leu Ile Asp Leu Ser Arg Tyr Ala Ser Lys Ile Asn Ile Gly
            660                 665                 670

Ser Lys Val Asn Phe Asp Pro Ile Asp Lys Asn Gln Ile Gln Leu Phe
            675                 680                 685

Asn Leu Glu Ser Ser Lys Ile Glu Val Ile Leu Lys Asn Ala Ile Val
            690                 695                 700

Tyr Asn Ser Met Tyr Glu Asn Phe Ser Thr Ser Phe Trp Ile Arg Ile
705                 710                 715                 720

Pro Lys Tyr Phe Asn Ser Ile Ser Leu Asn Asn Glu Tyr Thr Ile Ile
                725                 730                 735

Asn Cys Met Glu Asn Asn Ser Gly Trp Lys Val Ser Leu Asn Tyr Gly
            740                 745                 750

Glu Ile Ile Trp Thr Leu Gln Asp Thr Gln Glu Ile Lys Gln Arg Val
            755                 760                 765

Val Phe Lys Tyr Ser Gln Met Ile Asn Ile Ser Asp Tyr Ile Asn Arg
        770                 775                 780

Trp Ile Phe Val Thr Ile Thr Asn Asn Arg Leu Asn Asn Ser Lys Ile
785                 790                 795                 800
```

-continued

```
Tyr Ile Asn Gly Arg Leu Ile Asp Gln Lys Pro Ile Ser Asn Leu Gly
            805                 810                 815

Asn Ile His Ala Ser Asn Asn Ile Met Phe Lys Leu Asp Gly Cys Arg
        820                 825                 830

Asp Thr His Arg Tyr Ile Trp Ile Lys Tyr Phe Asn Leu Phe Asp Lys
            835                 840                 845

Glu Leu Asn Glu Lys Glu Ile Lys Asp Leu Tyr Asp Asn Gln Ser Asn
        850                 855                 860

Ser Gly Ile Leu Lys Asp Phe Trp Gly Asp Tyr Leu Gln Tyr Asp Lys
865                 870                 875                 880

Pro Tyr Tyr Met Leu Asn Leu Tyr Asp Pro Asn Lys Tyr Val Asp Val
                885                 890                 895

Asn Asn Val Gly Ile Arg Gly Tyr Met Tyr Leu Lys Gly Pro Arg Gly
            900                 905                 910

Ser Val Met Thr Thr Asn Ile Tyr Leu Asn Ser Ser Leu Tyr Arg Gly
        915                 920                 925

Thr Lys Phe Ile Ile Lys Lys Tyr Ala Ser Gly Asn Lys Asp Asn Ile
    930                 935                 940

Val Arg Asn Asn Asp Arg Val Tyr Ile Asn Val Val Val Lys Asn Lys
945                 950                 955                 960

Glu Tyr Arg Leu Ala Thr Asn Ala Ser Gln Ala Gly Val Glu Lys Ile
                965                 970                 975

Leu Ser Ala Leu Glu Ile Pro Asp Val Gly Asn Leu Ser Gln Val Val
            980                 985                 990

Val Met Lys Ser Lys Asn Asp Gln Gly Ile Thr Asn Lys Cys Lys Met
        995                 1000                1005

Asn Leu Gln Asp Asn Asn Gly Asn Asp Ile Gly Phe Ile Gly Phe His
    1010                1015                1020

Gln Phe Asn Asn Ile Ala Lys Leu Val Ala Ser Asn Trp Tyr Asn Arg
1025                1030                1035                1040

Gln Ile Glu Arg Ser Ser Arg Thr Leu Gly Cys Ser Trp Glu Phe Ile
                1045                1050                1055

Pro Val Asp Asp Gly Trp Gly Glu Arg Pro Leu
            1060                1065

<210> SEQ ID NO 4
<211> LENGTH: 1070
<212> TYPE: PRT
<213> ORGANISM: Artificial Sequence
<220> FEATURE:
<223> OTHER INFORMATION: Construct comprising Mn-SOD from B.
      stearothermophilus, a linker, and  a heavy chain from botulinium
      neurotoxin serotype B

<400> SEQUENCE: 4

Met Pro Phe Glu Leu Pro Ala Leu Pro Tyr Pro Tyr Asp Ala Leu Glu
1               5                   10                  15

Pro His Ile Asp Lys Glu Thr Met Asn Ile His His Thr Lys His His
            20                  25                  30

Asn Thr Tyr Val Thr Asn Leu Asn Ala Ala Leu Glu Gly His Pro Asp
        35                  40                  45

Leu Gln Asn Lys Ser Leu Glu Glu Leu Leu Ser Asn Leu Glu Ala Leu
    50                  55                  60

Pro Glu Ser Ile Arg Thr Ala Val Arg Asn Asn Gly Gly Gly His Ala
65                  70                  75                  80
```

-continued

```
Asn His Ser Leu Phe Trp Thr Ile Leu Ser Pro Asn Gly Gly Glu
             85                  90                  95

Pro Thr Gly Glu Leu Ala Asp Ala Ile Asn Lys Lys Phe Gly Ser Phe
            100                 105                 110

Thr Ala Phe Lys Asp Glu Phe Ser Lys Ala Ala Gly Arg Phe Gly
            115                 120                 125

Ser Gly Trp Ala Trp Leu Val Val Asn Asn Gly Glu Leu Glu Ile Thr
130                 135                 140

Ser Thr Pro Asn Gln Asp Ser Pro Ile Met Glu Gly Lys Thr Pro Ile
145                 150                 155                 160

Leu Gly Leu Asp Val Trp Glu His Ala Tyr Tyr Leu Lys Tyr Gln Asn
                165                 170                 175

Arg Arg Pro Glu Tyr Ile Ala Ala Phe Trp Asn Val Val Asn Trp Asp
            180                 185                 190

Glu Val Ala Lys Arg Tyr Ser Glu Ala Lys Ala Lys Gln Arg Ser Cys
            195                 200                 205

Gly Leu Val Pro Arg Gly Ser Gly Pro Gly Ser Lys Ala Pro Gly Ile
210                 215                 220

Cys Ile Asp Val Asp Asn Glu Asp Leu Phe Phe Ile Ala Asp Lys Asn
225                 230                 235                 240

Ser Phe Ser Asp Asp Leu Ser Lys Asn Glu Arg Ile Glu Tyr Asn Thr
            245                 250                 255

Gln Ser Asn Tyr Ile Glu Asn Asp Phe Pro Ile Asn Glu Leu Ile Leu
            260                 265                 270

Asp Thr Asp Leu Ile Ser Lys Ile Glu Leu Pro Ser Glu Asn Thr Glu
            275                 280                 285

Ser Leu Thr Asp Phe Asn Val Asp Val Pro Val Tyr Gly Lys Gln Pro
290                 295                 300

Ala Ile Lys Lys Ile Phe Thr Asp Glu Asn Thr Ile Phe Gln Tyr Leu
305                 310                 315                 320

Tyr Ser Gln Thr Phe Pro Leu Asp Ile Arg Asp Ile Ser Leu Thr Ser
            325                 330                 335

Ser Phe Asp Asp Ala Leu Leu Phe Ser Asn Lys Val Tyr Ser Phe Phe
            340                 345                 350

Ser Met Asp Tyr Ile Lys Thr Ala Asn Lys Val Val Glu Ala Gly Leu
            355                 360                 365

Phe Ala Gly Trp Val Lys Gln Ile Val Asn Asp Phe Val Ile Glu Ala
370                 375                 380

Asn Lys Ser Asn Thr Met Asp Lys Ile Ala Asp Ile Ser Leu Ile Val
385                 390                 395                 400

Pro Tyr Ile Gly Leu Ala Leu Asn Val Gly Asn Glu Thr Ala Lys Gly
            405                 410                 415

Asn Phe Glu Asn Ala Phe Glu Ile Ala Gly Ala Ser Ile Leu Leu Glu
            420                 425                 430

Phe Ile Pro Glu Leu Leu Ile Pro Val Val Gly Ala Phe Leu Leu Glu
            435                 440                 445

Ser Tyr Ile Asp Asn Lys Asn Lys Ile Ile Lys Thr Ile Asp Asn Ala
450                 455                 460

Leu Thr Lys Arg Asn Glu Lys Trp Ser Asp Met Tyr Gly Leu Ile Val
465                 470                 475                 480

Ala Gln Trp Leu Ser Thr Val Asn Thr Gln Phe Tyr Thr Ile Lys Glu
            485                 490                 495
```

```
Gly Met Tyr Lys Ala Leu Asn Tyr Gln Ala Gln Ala Leu Glu Glu Ile
            500                 505                 510

Ile Lys Tyr Arg Tyr Asn Ile Tyr Ser Glu Lys Glu Lys Ser Asn Ile
            515                 520                 525

Asn Ile Asp Phe Asn Asp Ile Asn Ser Lys Leu Asn Glu Gly Ile Asn
            530                 535                 540

Gln Ala Ile Asp Asn Ile Asn Asn Phe Ile Asn Gly Cys Ser Val Ser
545                 550                 555                 560

Tyr Leu Met Lys Lys Met Ile Pro Leu Ala Val Glu Lys Leu Leu Asp
                565                 570                 575

Phe Asp Asn Thr Leu Lys Lys Asn Leu Leu Asn Tyr Ile Asp Glu Asn
                580                 585                 590

Lys Leu Tyr Leu Ile Gly Ser Ala Glu Tyr Glu Lys Ser Lys Val Asn
                595                 600                 605

Lys Tyr Leu Lys Thr Ile Met Pro Phe Asp Leu Ser Ile Tyr Thr Asn
                610                 615                 620

Asp Thr Ile Leu Ile Glu Met Phe Asn Lys Tyr Asn Ser Glu Ile Leu
625                 630                 635                 640

Asn Asn Ile Ile Leu Asn Leu Arg Tyr Lys Asp Asn Asn Leu Ile Asp
                645                 650                 655

Leu Ser Gly Tyr Gly Ala Lys Val Glu Val Tyr Asp Gly Val Glu Leu
                660                 665                 670

Asn Asp Lys Asn Gln Phe Lys Leu Thr Ser Ser Ala Asn Ser Lys Ile
                675                 680                 685

Arg Val Thr Gln Asn Gln Asn Ile Ile Phe Asn Ser Val Phe Leu Asp
                690                 695                 700

Phe Ser Val Ser Phe Trp Ile Arg Ile Pro Lys Tyr Lys Asn Asp Gly
705                 710                 715                 720

Ile Gln Asn Tyr Ile His Asn Glu Tyr Thr Ile Ile Asn Cys Met Lys
                725                 730                 735

Asn Asn Ser Gly Trp Lys Ile Ser Ile Arg Gly Asn Arg Ile Ile Trp
                740                 745                 750

Thr Leu Ile Asp Ile Asn Gly Lys Thr Lys Ser Val Phe Phe Glu Tyr
                755                 760                 765

Asn Ile Arg Glu Asp Ile Ser Glu Tyr Ile Asn Arg Trp Phe Phe Val
                770                 775                 780

Thr Ile Thr Asn Asn Leu Asn Asn Ala Lys Ile Tyr Ile Asn Gly Lys
785                 790                 795                 800

Leu Glu Ser Asn Thr Asp Ile Lys Asp Ile Arg Glu Val Ile Ala Asn
                805                 810                 815

Gly Glu Ile Ile Phe Lys Leu Asp Gly Asp Ile Asp Arg Thr Gln Phe
                820                 825                 830

Ile Trp Met Lys Tyr Phe Ser Ile Phe Asn Thr Glu Leu Ser Gln Ser
                835                 840                 845

Asn Ile Glu Glu Arg Tyr Lys Ile Gln Ser Tyr Ser Glu Tyr Leu Lys
                850                 855                 860

Asp Phe Trp Gly Asn Pro Leu Met Tyr Asn Lys Glu Tyr Tyr Met Phe
865                 870                 875                 880

Asn Ala Gly Asn Lys Asn Ser Tyr Ile Lys Leu Lys Lys Asp Ser Pro
                885                 890                 895

Val Gly Glu Ile Leu Thr Arg Ser Lys Tyr Asn Gln Asn Ser Lys Tyr
                900                 905                 910
```

```
Ile Asn Tyr Arg Asp Leu Tyr Ile Gly Glu Lys Phe Ile Arg Arg
            915                 920                 925

Lys Ser Asn Ser Gln Ser Ile Asn Asp Asp Ile Val Arg Lys Glu Asp
        930                 935                 940

Tyr Ile Tyr Leu Asp Phe Phe Asn Leu Asn Gln Glu Trp Arg Val Tyr
945                 950                 955                 960

Thr Tyr Lys Tyr Phe Lys Lys Glu Glu Lys Leu Phe Leu Ala Pro
                965                 970                 975

Ile Ser Asp Ser Asp Glu Phe Tyr Asn Thr Ile Gln Ile Lys Glu Tyr
            980                 985                 990

Asp Glu Gln Pro Thr Tyr Ser Cys Gln Leu Leu Phe Lys Lys Asp Glu
        995                 1000                1005

Glu Ser Thr Asp Glu Ile Gly Leu Ile Gly Ile His Arg Phe Tyr Glu
    1010                1015                1020

Ser Gly Ile Val Phe Glu Glu Tyr Lys Asp Tyr Phe Cys Ile Ser Lys
1025                1030                1035                1040

Trp Tyr Leu Lys Glu Val Lys Arg Lys Pro Tyr Asn Leu Lys Leu Gly
                1045                1050                1055

Cys Asn Trp Gln Phe Ile Pro Lys Asp Glu Gly Trp Thr Glu
            1060                1065                1070

<210> SEQ ID NO 5
<211> LENGTH: 1059
<212> TYPE: PRT
<213> ORGANISM: Artificial Sequence
<220> FEATURE:
<223> OTHER INFORMATION: Construct comprising Mn-SOD from B.
      stearothermophilus, a linker, and a heavy chain from botulinium
      neurotoxin serotype F

<400> SEQUENCE: 5

Met Pro Phe Glu Leu Pro Ala Leu Pro Tyr Pro Tyr Asp Ala Leu Glu
  1               5                  10                  15

Pro His Ile Asp Lys Glu Thr Met Asn Ile His His Thr Lys His His
             20                  25                  30

Asn Thr Tyr Val Thr Asn Leu Asn Ala Ala Leu Glu Gly His Pro Asp
         35                  40                  45

Leu Gln Asn Lys Ser Leu Glu Glu Leu Leu Ser Asn Leu Glu Ala Leu
     50                  55                  60

Pro Glu Ser Ile Arg Thr Ala Val Arg Asn Asn Gly Gly Gly His Ala
 65                  70                  75                  80

Asn His Ser Leu Phe Trp Thr Ile Leu Ser Pro Asn Gly Gly Gly Glu
                 85                  90                  95

Pro Thr Gly Glu Leu Ala Asp Ala Ile Asn Lys Lys Phe Gly Ser Phe
            100                 105                 110

Thr Ala Phe Lys Asp Glu Phe Ser Lys Ala Ala Gly Arg Phe Gly
        115                 120                 125

Ser Gly Trp Ala Trp Leu Val Val Asn Asn Gly Glu Leu Glu Ile Thr
130                 135                 140

Ser Thr Pro Asn Gln Asp Ser Pro Ile Met Glu Gly Lys Thr Pro Ile
145                 150                 155                 160

Leu Gly Leu Asp Val Trp Glu His Ala Tyr Tyr Leu Lys Tyr Gln Asn
                165                 170                 175

Arg Arg Pro Glu Tyr Ile Ala Ala Phe Trp Asn Val Val Asn Trp Asp
            180                 185                 190
```

-continued

```
Glu Val Ala Lys Arg Tyr Ser Glu Ala Lys Ala Lys Gln Arg Ser Cys
            195                 200                 205

Gly Leu Val Pro Arg Gly Ser Gly Pro Gly Ser Lys Ala Pro Pro Arg
            210                 215                 220

Leu Cys Ile Arg Val Asn Asn Arg Glu Leu Phe Phe Val Ala Ser Glu
225                 230                 235                 240

Ser Ser Tyr Asn Glu Asn Asp Ile Asn Thr Pro Lys Glu Ile Asp Asp
            245                 250                 255

Thr Thr Asn Leu Asn Asn Asn Tyr Arg Asn Asn Leu Asp Glu Val Ile
            260                 265                 270

Leu Asp Tyr Asn Ser Glu Thr Ile Pro Gln Ile Ser Asn Gln Thr Leu
            275                 280                 285

Asn Thr Leu Val Gln Asp Asp Ser Tyr Val Pro Arg Tyr Asp Ser Asn
            290                 295                 300

Gly Thr Ser Glu Ile Glu Glu His Asn Val Val Asp Leu Asn Val Phe
305                 310                 315                 320

Phe Tyr Leu His Ala Gln Lys Val Pro Glu Gly Glu Thr Asn Ile Ser
            325                 330                 335

Leu Thr Ser Ser Ile Asp Thr Ala Leu Ser Glu Glu Ser Gln Val Tyr
            340                 345                 350

Thr Phe Phe Ser Ser Glu Phe Ile Asn Thr Ile Asn Lys Pro Val His
            355                 360                 365

Ala Ala Leu Phe Ile Ser Trp Ile Asn Gln Val Ile Arg Asp Phe Thr
            370                 375                 380

Thr Glu Ala Thr Gln Lys Ser Thr Phe Asp Lys Ile Ala Asp Ile Ser
385                 390                 395                 400

Leu Val Val Pro Tyr Val Gly Leu Ala Leu Asn Ile Gly Asn Glu Val
            405                 410                 415

Gln Lys Glu Asn Phe Lys Glu Ala Phe Glu Leu Leu Gly Ala Gly Ile
            420                 425                 430

Leu Leu Glu Phe Val Pro Glu Leu Leu Ile Pro Thr Ile Leu Val Phe
            435                 440                 445

Thr Ile Lys Ser Phe Ile Gly Ser Ser Glu Asn Lys Asn Lys Ile Ile
450                 455                 460

Lys Ala Ile Asn Asn Ser Leu Met Glu Arg Glu Thr Lys Trp Lys Glu
465                 470                 475                 480

Ile Tyr Ser Trp Ile Val Ser Asn Trp Leu Thr Arg Ile Asn Thr Gln
            485                 490                 495

Phe Asn Lys Arg Lys Glu Gln Met Tyr Gln Ala Leu Gln Asn Gln Val
            500                 505                 510

Asp Ala Ile Lys Thr Val Ile Glu Tyr Lys Tyr Asn Asn Tyr Thr Ser
            515                 520                 525

Asp Glu Arg Asn Arg Leu Glu Ser Glu Tyr Asn Ile Asn Asn Ile Arg
            530                 535                 540

Glu Glu Leu Asn Lys Lys Val Ser Leu Ala Met Glu Asn Ile Glu Arg
545                 550                 555                 560

Phe Ile Thr Glu Ser Ser Ile Phe Tyr Leu Met Lys Leu Ile Asn Glu
            565                 570                 575

Ala Lys Val Ser Lys Leu Arg Glu Tyr Asp Glu Gly Val Lys Glu Tyr
            580                 585                 590

Leu Leu Asp Tyr Ile Ser Glu His Arg Ser Ile Leu Gly Asn Ser Val
            595                 600                 605
```

-continued

```
Gln Glu Leu Asn Asp Leu Val Thr Ser Thr Leu Asn Ser Ile Pro
    610                 615                 620

Phe Glu Leu Ser Ser Tyr Thr Asn Asp Lys Ile Leu Ile Leu Tyr Phe
625                 630                 635                 640

Asn Lys Leu Tyr Lys Lys Ile Lys Asp Asn Ser Ile Leu Asp Met Arg
                645                 650                 655

Tyr Glu Asn Asn Lys Phe Ile Asp Ile Ser Gly Tyr Gly Ser Asn Ile
                660                 665                 670

Ser Ile Asn Gly Asp Val Tyr Ile Tyr Ser Thr Asn Arg Asn Gln Phe
            675                 680                 685

Gly Ile Tyr Ser Ser Lys Pro Ser Glu Val Asn Ile Ala Gln Asn Asn
        690                 695                 700

Asp Ile Ile Tyr Asn Gly Arg Tyr Gln Asn Phe Ser Ile Ser Phe Trp
705                 710                 715                 720

Val Arg Ile Pro Lys Tyr Phe Asn Lys Val Asn Leu Asn Asn Glu Tyr
                725                 730                 735

Thr Ile Ile Asp Cys Ile Arg Asn Asn Asn Ser Gly Trp Lys Ile Ser
                740                 745                 750

Leu Asn Tyr Asn Lys Ile Ile Trp Thr Leu Gln Asp Thr Ala Gly Asn
            755                 760                 765

Asn Gln Lys Leu Val Phe Asn Tyr Thr Gln Met Ile Ser Ile Ser Asp
        770                 775                 780

Tyr Ile Asn Lys Trp Ile Phe Val Thr Ile Thr Asn Asn Arg Leu Gly
785                 790                 795                 800

Asn Ser Arg Ile Tyr Ile Asn Gly Asn Leu Ile Asp Glu Lys Ser Ile
                805                 810                 815

Ser Asn Leu Gly Asp Ile His Val Ser Asp Asn Ile Leu Phe Lys Ile
            820                 825                 830

Val Gly Cys Asn Asp Thr Arg Tyr Val Gly Ile Arg Tyr Phe Lys Val
        835                 840                 845

Phe Asp Thr Glu Leu Gly Lys Thr Glu Ile Glu Thr Leu Tyr Ser Asp
850                 855                 860

Glu Pro Asp Pro Ser Ile Leu Lys Asp Phe Trp Gly Asn Tyr Leu Leu
865                 870                 875                 880

Tyr Asn Lys Arg Tyr Tyr Leu Leu Asn Leu Leu Arg Thr Asp Lys Ser
                885                 890                 895

Ile Thr Gln Asn Ser Asn Phe Leu Asn Ile Asn Gln Gln Arg Gly Val
            900                 905                 910

Tyr Gln Lys Pro Asn Ile Phe Ser Asn Thr Arg Leu Tyr Thr Gly Val
        915                 920                 925

Glu Val Ile Ile Arg Lys Asn Gly Ser Thr Asp Ile Ser Asn Thr Asp
    930                 935                 940

Asn Phe Val Arg Lys Asn Asp Leu Ala Tyr Ile Asn Val Val Asp Arg
945                 950                 955                 960

Asp Val Glu Tyr Arg Leu Tyr Ala Asp Ile Ser Ile Ala Lys Pro Glu
                965                 970                 975

Lys Ile Ile Lys Leu Ile Arg Thr Ser Asn Ser Asn Asn Ser Leu Gly
            980                 985                 990

Gln Ile Ile Val Met Asp Ser Ile Gly Asn Asn Cys Thr Met Asn Phe
        995                 1000                1005

Gln Asn Asn Asn Gly Gly Asn Ile Gly Leu Leu Gly Phe His Ser Asn
    1010                1015                1020
```

-continued

```
Asn Leu Val Ala Ser Ser Trp Tyr Tyr Asn Asn Ile Arg Lys Asn Thr
1025                1030                1035                1040

Ser Ser Asn Gly Cys Phe Trp Ser Phe Ile Ser Lys Glu His Gly Trp
            1045                1050                1055

Gln Glu Asn

<210> SEQ ID NO 6
<211> LENGTH: 1092
<212> TYPE: PRT
<213> ORGANISM: Artificial Sequence
<220> FEATURE:
<223> OTHER INFORMATION: Construct comprising a mitochondrial leader
      sequence from Human Mn- SOD, Mn-SOD from B. stearothermophilus, a
      linker, and a heavy chain  from  botulinium neurotoxin  serotype A

<400> SEQUENCE: 6

Met Leu Ser Arg Ala Val Cys Gly Thr Ser Arg Gln Leu Ala Pro Ala
 1               5                  10                  15

Leu Gly Tyr Leu Gly Ser Arg Gln Lys His Ser Arg Gly Ser Pro Ala
            20                  25                  30

Leu Pro Tyr Pro Tyr Asp Ala Leu Glu Pro His Ile Asp Lys Glu Thr
            35                  40                  45

Met Asn Ile His His Thr Lys His His Asn Thr Tyr Val Thr Asn Leu
50                  55                  60

Asn Ala Ala Leu Glu Gly His Pro Asp Leu Gln Asn Lys Ser Leu Glu
65                  70                  75                  80

Glu Leu Leu Ser Asn Leu Glu Ala Leu Pro Glu Ser Ile Arg Thr Ala
                85                  90                  95

Val Arg Asn Asn Gly Gly Gly His Ala Asn His Ser Leu Phe Trp Thr
            100                 105                 110

Ile Leu Ser Pro Asn Gly Gly Gly Glu Pro Thr Gly Glu Leu Ala Asp
            115                 120                 125

Ala Ile Asn Lys Lys Phe Gly Ser Phe Thr Ala Phe Lys Asp Glu Phe
130                 135                 140

Ser Lys Ala Ala Ala Gly Arg Phe Gly Ser Gly Trp Ala Trp Leu Val
145                 150                 155                 160

Val Asn Asn Gly Glu Leu Glu Ile Thr Ser Thr Pro Asn Gln Asp Ser
                165                 170                 175

Pro Ile Met Glu Gly Lys Thr Pro Ile Leu Gly Leu Asp Val Trp Glu
            180                 185                 190

His Ala Tyr Tyr Leu Lys Tyr Gln Asn Arg Arg Pro Glu Tyr Ile Ala
            195                 200                 205

Ala Phe Trp Asn Val Val Asn Trp Asp Glu Val Ala Lys Arg Tyr Ser
210                 215                 220

Glu Ala Lys Ala Lys Gln Arg Ser Cys Gly Leu Val Pro Arg Gly Ser
225                 230                 235                 240

Gly Pro Gly Ser Ala Leu Asn Asp Leu Cys Ile Lys Val Asn Asn Trp
                245                 250                 255

Asp Leu Phe Phe Ser Pro Ser Glu Asp Asn Phe Thr Asn Asp Leu Asn
            260                 265                 270

Lys Gly Glu Glu Ile Thr Ser Asp Thr Asn Ile Glu Ala Ala Glu Glu
            275                 280                 285

Asn Ile Ser Leu Asp Leu Ile Gln Gln Tyr Tyr Leu Thr Phe Asn Phe
290                 295                 300

Asp Asn Glu Pro Glu Asn Ile Ser Ile Glu Asn Leu Ser Ser Asp Ile
305                 310                 315                 320
```

```
Ile Gly Gln Leu Glu Leu Met Pro Asn Ile Glu Arg Phe Pro Asn Gly
            325                 330                 335
Lys Lys Tyr Glu Leu Asp Lys Tyr Thr Met Phe His Tyr Leu Arg Ala
            340                 345                 350
Gln Glu Phe Glu His Gly Lys Ser Arg Ile Ala Leu Thr Asn Ser Val
            355                 360                 365
Asn Glu Ala Leu Leu Asn Pro Ser Arg Val Tyr Thr Phe Phe Ser Ser
    370                 375                 380
Asp Tyr Val Lys Lys Val Asn Lys Ala Thr Glu Ala Ala Met Phe Leu
385                 390                 395                 400
Gly Trp Val Glu Gln Leu Val Tyr Asp Phe Thr Asp Glu Thr Ser Glu
                405                 410                 415
Val Ser Thr Thr Asp Lys Ile Ala Asp Ile Thr Ile Ile Pro Tyr
            420                 425                 430
Ile Gly Pro Ala Leu Asn Ile Gly Asn Met Leu Tyr Lys Asp Asp Phe
            435                 440                 445
Val Gly Ala Leu Ile Phe Ser Gly Ala Val Ile Leu Leu Glu Phe Ile
            450                 455                 460
Pro Glu Ile Ala Ile Pro Val Leu Gly Thr Phe Ala Leu Val Ser Tyr
465                 470                 475                 480
Ile Ala Asn Lys Val Leu Thr Val Gln Thr Ile Asp Asn Ala Leu Ser
                485                 490                 495
Lys Arg Asn Glu Lys Trp Asp Glu Val Tyr Lys Tyr Ile Val Thr Asn
            500                 505                 510
Trp Leu Ala Lys Val Asn Thr Gln Ile Asp Leu Ile Arg Lys Lys Met
            515                 520                 525
Lys Glu Ala Leu Glu Asn Gln Ala Glu Ala Thr Lys Ala Ile Ile Asn
    530                 535                 540
Tyr Gln Tyr Asn Gln Tyr Thr Glu Glu Lys Asn Asn Ile Asn Phe
545                 550                 555                 560
Asn Ile Asp Asp Leu Ser Ser Lys Leu Asn Glu Ser Ile Asn Lys Ala
            565                 570                 575
Met Ile Asn Ile Asn Lys Phe Leu Asn Gln Cys Ser Val Ser Tyr Leu
            580                 585                 590
Met Asn Ser Met Ile Pro Tyr Gly Val Lys Arg Leu Glu Asp Phe Asp
            595                 600                 605
Ala Ser Leu Lys Asp Ala Leu Leu Lys Tyr Ile Tyr Asp Asn Arg Gly
    610                 615                 620
Thr Leu Ile Gly Gln Val Asp Arg Leu Lys Asp Lys Val Asn Asn Thr
625                 630                 635                 640
Leu Ser Thr Asp Ile Pro Phe Gln Leu Ser Lys Tyr Val Asp Asn Gln
                645                 650                 655
Arg Leu Leu Ser Thr Phe Thr Glu Tyr Ile Lys Asn Ile Ile Asn Thr
            660                 665                 670
Ser Ile Leu Asn Leu Arg Tyr Glu Ser Asn His Leu Ile Asp Leu Ser
            675                 680                 685
Arg Tyr Ala Ser Lys Ile Asn Ile Gly Ser Lys Val Asn Phe Asp Pro
    690                 695                 700
Ile Asp Lys Asn Gln Ile Gln Leu Phe Asn Leu Glu Ser Ser Lys Ile
705                 710                 715                 720
Glu Val Ile Leu Lys Asn Ala Ile Val Tyr Asn Ser Met Tyr Glu Asn
                725                 730                 735
```

```
Phe Ser Thr Ser Phe Trp Ile Arg Ile Pro Lys Tyr Phe Asn Ser Ile
            740                 745                 750
Ser Leu Asn Asn Glu Tyr Thr Ile Ile Asn Cys Met Glu Asn Asn Ser
            755                 760             765
Gly Trp Lys Val Ser Leu Asn Tyr Gly Glu Ile Ile Trp Thr Leu Gln
            770                 775                 780
Asp Thr Gln Glu Ile Lys Gln Arg Val Val Phe Lys Tyr Ser Gln Met
785                 790                 795                 800
Ile Asn Ile Ser Asp Tyr Ile Asn Arg Trp Ile Phe Val Thr Ile Thr
                805                 810                 815
Asn Asn Arg Leu Asn Asn Ser Lys Ile Tyr Ile Asn Gly Arg Leu Ile
            820                 825                 830
Asp Gln Lys Pro Ile Ser Asn Leu Gly Asn Ile His Ala Ser Asn Asn
            835                 840                 845
Ile Met Phe Lys Leu Asp Gly Cys Arg Asp Thr His Arg Tyr Ile Trp
            850                 855                 860
Ile Lys Tyr Phe Asn Leu Phe Asp Lys Glu Leu Asn Glu Lys Glu Ile
865                 870                 875                 880
Lys Asp Leu Tyr Asp Asn Gln Ser Asn Ser Gly Ile Leu Lys Asp Phe
                885                 890                 895
Trp Gly Asp Tyr Leu Gln Tyr Asp Lys Pro Tyr Tyr Met Leu Asn Leu
            900                 905                 910
Tyr Asp Pro Asn Lys Tyr Val Asp Val Asn Asn Val Gly Ile Arg Gly
            915                 920                 925
Tyr Met Tyr Leu Lys Gly Pro Arg Gly Ser Val Met Thr Thr Asn Ile
            930                 935                 940
Tyr Leu Asn Ser Ser Leu Tyr Arg Gly Thr Lys Phe Ile Ile Lys Lys
945                 950                 955                 960
Tyr Ala Ser Gly Asn Lys Asp Asn Ile Val Arg Asn Asn Asp Arg Val
                965                 970                 975
Tyr Ile Asn Val Val Val Lys Asn Lys Glu Tyr Arg Leu Ala Thr Asn
            980                 985                 990
Ala Ser Gln Ala Gly Val Glu Lys Ile Leu Ser Ala Leu Glu Ile Pro
            995                 1000                1005
Asp Val Gly Asn Leu Ser Gln Val Val Val Met Lys Ser Lys Asn Asp
    1010                1015                1020
Gln Gly Ile Thr Asn Lys Cys Lys Met Asn Leu Gln Asp Asn Asn Gly
1025                1030                1035                1040
Asn Asp Ile Gly Phe Ile Gly Phe His Gln Phe Asn Asn Ile Ala Lys
                1045                1050                1055
Leu Val Ala Ser Asn Trp Tyr Asn Arg Gln Ile Glu Arg Ser Ser Arg
            1060                1065                1070
Thr Leu Gly Cys Ser Trp Glu Phe Ile Pro Val Asp Asp Gly Trp Gly
        1075                1080                1085
Glu Arg Pro Leu
    1090
```

<210> SEQ ID NO 7
<211> LENGTH: 1095
<212> TYPE: PRT
<213> ORGANISM: Artificial Sequence
<220> FEATURE:
<223> OTHER INFORMATION: Construct comprising a mitochondrial leader
      sequence from Human Mn- SOD, Mn-SOD from B. stearothermophilus, a
      linker, and a heavy chain from botulinium neurotoxin serotype B

<400> SEQUENCE: 7

```
Met Leu Ser Arg Ala Val Cys Gly Thr Ser Arg Gln Leu Ala Pro Ala
 1               5                  10                  15

Leu Gly Tyr Leu Gly Ser Arg Gln Lys His Ser Arg Gly Ser Pro Ala
             20                  25                  30

Leu Pro Tyr Pro Tyr Asp Ala Leu Glu Pro His Ile Asp Lys Glu Thr
         35                  40                  45

Met Asn Ile His His Thr Lys His Asn Thr Tyr Val Thr Asn Leu
     50                  55                  60

Asn Ala Ala Leu Glu Gly His Pro Asp Leu Gln Asn Lys Ser Leu Glu
 65                  70                  75                  80

Glu Leu Leu Ser Asn Leu Glu Ala Leu Pro Glu Ser Ile Arg Thr Ala
                 85                  90                  95

Val Arg Asn Asn Gly Gly His Ala Asn His Ser Leu Phe Trp Thr
             100                 105                 110

Ile Leu Ser Pro Asn Gly Gly Glu Pro Thr Gly Glu Leu Ala Asp
             115                 120                 125

Ala Ile Asn Lys Lys Phe Gly Ser Phe Thr Ala Phe Lys Asp Glu Phe
     130                 135                 140

Ser Lys Ala Ala Ala Gly Arg Phe Gly Ser Gly Trp Ala Trp Leu Val
145                 150                 155                 160

Val Asn Asn Gly Glu Leu Glu Ile Thr Ser Thr Pro Asn Gln Asp Ser
                 165                 170                 175

Pro Ile Met Glu Gly Lys Thr Pro Ile Leu Gly Leu Asp Val Trp Glu
             180                 185                 190

His Ala Tyr Tyr Leu Lys Tyr Gln Asn Arg Arg Pro Glu Tyr Ile Ala
         195                 200                 205

Ala Phe Trp Asn Val Val Asn Trp Asp Glu Val Ala Lys Arg Tyr Ser
     210                 215                 220

Glu Ala Lys Ala Lys Gln Arg Ser Cys Gly Leu Val Pro Arg Gly Ser
225                 230                 235                 240

Gly Pro Gly Ser Lys Ala Pro Gly Ile Cys Ile Asp Val Asp Asn Glu
                 245                 250                 255

Asp Leu Phe Phe Ile Ala Asp Lys Asn Ser Phe Ser Asp Asp Leu Ser
             260                 265                 270

Lys Asn Glu Arg Ile Glu Tyr Asn Thr Gln Ser Asn Tyr Ile Glu Asn
         275                 280                 285

Asp Phe Pro Ile Asn Glu Leu Ile Leu Asp Thr Asp Leu Ile Ser Lys
     290                 295                 300

Ile Glu Leu Pro Ser Glu Asn Thr Glu Ser Leu Thr Asp Phe Asn Val
305                 310                 315                 320

Asp Val Pro Val Tyr Glu Lys Gln Pro Ala Ile Lys Lys Ile Phe Thr
                 325                 330                 335

Asp Glu Asn Thr Ile Phe Gln Tyr Leu Tyr Ser Gln Thr Phe Pro Leu
             340                 345                 350

Asp Ile Arg Asp Ile Ser Leu Thr Ser Ser Phe Asp Asp Ala Leu Leu
         355                 360                 365

Phe Ser Asn Lys Val Tyr Ser Phe Ser Met Asp Tyr Ile Lys Thr
     370                 375                 380

Ala Asn Lys Val Val Glu Ala Gly Leu Phe Ala Gly Trp Val Lys Gln
385                 390                 395                 400

Ile Val Asn Asp Phe Val Ile Glu Ala Asn Lys Ser Asn Thr Met Asp
                 405                 410                 415
```

-continued

```
Lys Ile Ala Asp Ile Ser Leu Ile Val Pro Tyr Ile Gly Leu Ala Leu
            420                 425                 430

Asn Val Gly Asn Glu Thr Ala Lys Gly Asn Phe Glu Asn Ala Phe Glu
            435                 440                 445

Ile Ala Gly Ala Ser Ile Leu Leu Glu Phe Ile Pro Glu Leu Leu Ile
        450                 455                 460

Pro Val Val Gly Ala Phe Leu Leu Glu Ser Tyr Ile Asp Asn Lys Asn
465                 470                 475                 480

Lys Ile Ile Lys Thr Ile Asp Asn Ala Leu Thr Lys Arg Asn Glu Lys
                485                 490                 495

Trp Ser Asp Met Tyr Gly Leu Ile Val Ala Gln Trp Leu Ser Thr Val
            500                 505                 510

Asn Thr Gln Phe Tyr Thr Ile Lys Glu Gly Met Tyr Lys Ala Leu Asn
            515                 520                 525

Tyr Gln Ala Gln Ala Leu Glu Glu Ile Ile Lys Tyr Arg Tyr Asn Ile
        530                 535                 540

Tyr Ser Glu Lys Glu Lys Ser Asn Ile Asn Ile Asp Phe Asn Asp Ile
545                 550                 555                 560

Asn Ser Lys Leu Asn Glu Gly Ile Asn Gln Ala Ile Asp Asn Ile Asn
                565                 570                 575

Asn Phe Ile Asn Gly Cys Ser Val Ser Tyr Leu Met Lys Lys Met Ile
            580                 585                 590

Pro Leu Ala Val Glu Lys Leu Leu Asp Phe Asp Asn Thr Leu Lys Lys
        595                 600                 605

Asn Leu Leu Asn Tyr Ile Asp Glu Asn Lys Leu Tyr Leu Ile Gly Ser
        610                 615                 620

Ala Glu Tyr Glu Lys Ser Lys Val Asn Lys Tyr Leu Lys Thr Ile Met
625                 630                 635                 640

Pro Phe Asp Leu Ser Ile Tyr Thr Asn Asp Thr Ile Leu Ile Glu Met
                645                 650                 655

Phe Asn Lys Tyr Asn Ser Glu Ile Leu Asn Asn Ile Ile Leu Asn Leu
            660                 665                 670

Arg Tyr Lys Asp Asn Asn Leu Ile Asp Leu Ser Gly Tyr Gly Ala Lys
        675                 680                 685

Val Glu Val Tyr Asp Gly Val Glu Leu Asn Asp Lys Asn Gln Phe Lys
690                 695                 700

Leu Thr Ser Ser Ala Asn Ser Lys Ile Arg Val Thr Gln Asn Gln Asn
705                 710                 715                 720

Ile Ile Phe Asn Ser Val Phe Leu Asp Phe Ser Val Ser Phe Trp Ile
                725                 730                 735

Arg Ile Pro Lys Tyr Lys Asn Asp Gly Ile Gln Asn Tyr Ile His Asn
            740                 745                 750

Glu Tyr Thr Ile Ile Asn Cys Met Lys Asn Asn Ser Gly Trp Lys Ile
            755                 760                 765

Ser Ile Arg Gly Asn Arg Ile Ile Trp Thr Leu Ile Asp Ile Asn Gly
        770                 775                 780

Lys Thr Lys Ser Val Phe Phe Glu Tyr Asn Ile Arg Glu Asp Ile Ser
785                 790                 795                 800

Glu Tyr Ile Asn Arg Trp Phe Phe Val Thr Ile Thr Asn Asn Leu Asn
                805                 810                 815

Asn Ala Lys Ile Tyr Ile Asn Gly Lys Leu Glu Ser Asn Thr Asp Ile
            820                 825                 830
```

```
Lys Asp Ile Arg Glu Val Ile Ala Asn Gly Glu Ile Ile Phe Lys Leu
            835                 840                 845

Asp Gly Asp Ile Asp Arg Thr Gln Phe Ile Trp Met Lys Tyr Phe Ser
        850                 855                 860

Ile Phe Asn Thr Glu Leu Ser Gln Ser Asn Ile Glu Glu Arg Tyr Lys
865                 870                 875                 880

Ile Gln Ser Tyr Ser Glu Tyr Leu Lys Asp Phe Trp Gly Asn Pro Leu
                885                 890                 895

Met Tyr Asn Lys Glu Tyr Tyr Met Phe Asn Ala Gly Asn Lys Asn Ser
            900                 905                 910

Tyr Ile Lys Leu Lys Lys Asp Ser Pro Val Gly Glu Ile Leu Thr Arg
        915                 920                 925

Ser Lys Tyr Asn Gln Asn Ser Lys Tyr Ile Asn Tyr Arg Asp Leu Tyr
    930                 935                 940

Ile Gly Glu Lys Phe Ile Ile Arg Arg Lys Ser Asn Ser Gln Ser Ile
945                 950                 955                 960

Asn Asp Asp Ile Val Arg Lys Glu Asp Tyr Ile Tyr Leu Asp Phe Phe
                965                 970                 975

Asn Leu Asn Gln Glu Trp Arg Val Tyr Thr Tyr Lys Tyr Phe Lys Lys
            980                 985                 990

Glu Glu Glu Lys Leu Phe Leu Ala Pro Ile Ser Asp Ser Asp Glu Phe
        995                 1000                1005

Tyr Asn Thr Ile Gln Ile Lys Glu Tyr Asp Glu Gln Pro Thr Tyr Ser
    1010                1015                1020

Cys Gln Leu Leu Phe Lys Lys Asp Glu Glu Ser Thr Asp Glu Ile Gly
1025                1030                1035                1040

Leu Ile Gly Ile His Arg Phe Tyr Glu Ser Gly Ile Val Phe Glu Glu
                1045                1050                1055

Tyr Lys Asp Tyr Phe Cys Ile Ser Lys Trp Tyr Leu Lys Glu Val Lys
            1060                1065                1070

Arg Lys Pro Tyr Asn Leu Lys Leu Gly Cys Asn Trp Gln Phe Ile Pro
        1075                1080                1085

Lys Asp Glu Gly Trp Thr Glu
    1090                1095

<210> SEQ ID NO 8
<211> LENGTH: 1084
<212> TYPE: PRT
<213> ORGANISM: Artificial Sequence
<220> FEATURE:
<223> OTHER INFORMATION: Construct comprising a mitochondrial leader
      sequence from Human Mn- SOD, Mn-SOD from B. stearothermophilus, a
      linker,

<400> SEQUENCE: 8

Met Leu Ser Arg Ala Val Cys Gly Thr Ser Arg Gln Leu Ala Pro Ala
1               5                   10                  15

Leu Gly Tyr Leu Gly Ser Arg Gln Lys His Ser Arg Gly Ser Pro Ala
            20                  25                  30

Leu Pro Tyr Pro Tyr Asp Ala Leu Glu Pro His Ile Asp Lys Glu Thr
        35                  40                  45

Met Asn Ile His His Thr Lys His His Asn Thr Tyr Val Thr Asn Leu
    50                  55                  60

Asn Ala Ala Leu Glu Gly His Pro Asp Leu Gln Asn Lys Ser Leu Glu
65                  70                  75                  80
```

```
Glu Leu Leu Ser Asn Leu Glu Ala Leu Pro Glu Ser Ile Arg Thr Ala
                85                  90                  95

Val Arg Asn Asn Gly Gly His Ala Asn His Ser Leu Phe Trp Thr
            100                 105                 110

Ile Leu Ser Pro Asn Gly Gly Glu Pro Thr Gly Glu Leu Ala Asp
            115                 120                 125

Ala Ile Asn Lys Lys Phe Gly Ser Phe Thr Ala Phe Lys Asp Glu Phe
            130                 135                 140

Ser Lys Ala Ala Ala Gly Arg Phe Gly Ser Gly Trp Ala Trp Leu Val
145                 150                 155                 160

Val Asn Asn Gly Glu Leu Glu Ile Thr Ser Thr Pro Asn Gln Asp Ser
                165                 170                 175

Pro Ile Met Glu Gly Lys Thr Pro Ile Leu Gly Leu Asp Val Trp Glu
            180                 185                 190

His Ala Tyr Tyr Leu Lys Tyr Gln Asn Arg Arg Pro Glu Tyr Ile Ala
            195                 200                 205

Ala Phe Trp Asn Val Val Asn Trp Asp Glu Val Ala Lys Arg Tyr Ser
            210                 215                 220

Glu Ala Lys Ala Lys Gln Arg Ser Cys Gly Leu Val Pro Arg Gly Ser
225                 230                 235                 240

Gly Pro Gly Ser Lys Ala Pro Pro Arg Leu Cys Ile Arg Val Asn Asn
                245                 250                 255

Arg Glu Leu Phe Phe Val Ala Ser Glu Ser Ser Tyr Asn Glu Asn Asp
            260                 265                 270

Ile Asn Thr Pro Lys Glu Ile Asp Asp Thr Thr Asn Leu Asn Asn Asn
            275                 280                 285

Tyr Arg Asn Asn Leu Asp Glu Val Ile Leu Asp Tyr Asn Ser Glu Thr
            290                 295                 300

Ile Pro Gln Ile Ser Asn Gln Thr Leu Asn Thr Leu Val Gln Asp Asp
305                 310                 315                 320

Ser Tyr Val Pro Arg Tyr Asp Ser Asn Gly Thr Ser Glu Ile Glu Glu
                325                 330                 335

His Asn Val Val Asp Leu Asn Val Phe Phe Tyr Leu His Ala Gln Lys
            340                 345                 350

Val Pro Glu Gly Glu Thr Asn Ile Ser Leu Thr Ser Ser Ile Asp Thr
            355                 360                 365

Ala Leu Ser Glu Glu Ser Gln Val Tyr Thr Phe Phe Ser Ser Glu Phe
            370                 375                 380

Ile Asn Thr Ile Asn Lys Pro Val His Ala Ala Leu Phe Ile Ser Trp
385                 390                 395                 400

Ile Asn Gln Val Ile Arg Asp Phe Thr Thr Glu Ala Thr Gln Lys Ser
                405                 410                 415

Thr Phe Asp Lys Ile Ala Asp Ile Ser Leu Val Val Pro Tyr Val Gly
            420                 425                 430

Leu Ala Leu Asn Ile Gly Asn Glu Val Gln Lys Glu Asn Phe Lys Glu
            435                 440                 445

Ala Phe Glu Leu Leu Gly Ala Gly Ile Leu Leu Glu Phe Val Pro Glu
            450                 455                 460

Leu Leu Ile Pro Thr Ile Leu Val Phe Thr Ile Lys Ser Phe Ile Gly
465                 470                 475                 480

Ser Ser Glu Asn Lys Asn Lys Ile Ile Lys Ala Ile Asn Asn Ser Leu
                485                 490                 495
```

```
Met Glu Arg Glu Thr Lys Trp Lys Glu Ile Tyr Ser Trp Ile Val Ser
                500             505             510

Asn Trp Leu Thr Arg Ile Asn Thr Gln Phe Asn Lys Arg Lys Glu Gln
        515             520             525

Met Tyr Gln Ala Leu Gln Asn Gln Val Asp Ala Ile Lys Thr Val Ile
    530             535             540

Glu Tyr Lys Tyr Asn Asn Tyr Thr Ser Asp Glu Arg Asn Arg Leu Glu
545             550             555             560

Ser Glu Tyr Asn Ile Asn Asn Ile Arg Glu Glu Leu Asn Lys Lys Val
            565             570             575

Ser Leu Ala Met Glu Asn Ile Glu Arg Phe Ile Thr Glu Ser Ser Ile
            580             585             590

Phe Tyr Leu Met Lys Leu Ile Asn Glu Ala Lys Val Ser Lys Leu Arg
            595             600             605

Glu Tyr Asp Glu Gly Val Lys Glu Tyr Leu Leu Asp Tyr Ile Ser Glu
            610             615             620

His Arg Ser Ile Leu Gly Asn Ser Val Gln Glu Leu Asn Asp Leu Val
625             630             635             640

Thr Ser Thr Leu Asn Asn Ser Ile Pro Phe Glu Leu Ser Ser Tyr Thr
                645             650             655

Asn Asp Lys Ile Leu Ile Leu Tyr Phe Asn Lys Leu Tyr Lys Lys Ile
            660             665             670

Lys Asp Asn Ser Ile Leu Asp Met Arg Tyr Glu Asn Asn Lys Phe Ile
            675             680             685

Asp Ile Ser Gly Tyr Gly Ser Asn Ile Ser Ile Asn Gly Asp Val Tyr
            690             695             700

Ile Tyr Ser Thr Asn Arg Asn Gln Phe Gly Ile Tyr Ser Ser Lys Pro
705             710             715             720

Ser Glu Val Asn Ile Ala Gln Asn Asn Asp Ile Ile Tyr Asn Gly Arg
                725             730             735

Tyr Gln Asn Phe Ser Ile Ser Phe Trp Val Arg Ile Pro Lys Tyr Phe
            740             745             750

Asn Lys Val Asn Leu Asn Asn Glu Tyr Thr Ile Ile Asp Cys Ile Arg
            755             760             765

Asn Asn Asn Ser Gly Trp Lys Ile Ser Leu Asn Tyr Asn Lys Ile Ile
            770             775             780

Trp Thr Leu Gln Asp Thr Ala Gly Asn Asn Gln Lys Leu Val Phe Asn
785             790             795             800

Tyr Thr Gln Met Ile Ser Ile Ser Asp Tyr Ile Asn Lys Trp Ile Phe
                805             810             815

Val Thr Ile Thr Asn Asn Arg Leu Gly Asn Ser Arg Ile Tyr Ile Asn
            820             825             830

Gly Asn Leu Ile Asp Glu Lys Ser Ile Ser Asn Leu Gly Asp Ile His
            835             840             845

Val Ser Asp Asn Ile Leu Phe Lys Ile Val Gly Cys Asn Asp Thr Arg
850             855             860

Tyr Val Gly Ile Arg Tyr Phe Lys Val Phe Asp Thr Glu Leu Gly Lys
865             870             875             880

Thr Glu Ile Glu Thr Leu Tyr Ser Asp Glu Pro Asp Pro Ser Ile Leu
                885             890             895

Lys Asp Phe Trp Gly Asn Tyr Leu Leu Tyr Asn Lys Arg Tyr Tyr Leu
            900             905             910
```

```
Leu Asn Leu Leu Arg Thr Asp Lys Ser Ile Thr Gln Asn Ser Asn Phe
        915                 920                 925

Leu Asn Ile Asn Gln Gln Arg Gly Val Tyr Gln Lys Pro Asn Ile Phe
        930                 935                 940

Ser Asn Thr Arg Leu Tyr Thr Gly Val Glu Val Ile Arg Lys Asn
945                 950                 955                 960

Gly Ser Thr Asp Ile Ser Asn Thr Asp Asn Phe Val Arg Lys Asn Asp
                965                 970                 975

Leu Ala Tyr Ile Asn Val Val Asp Arg Asp Val Glu Tyr Arg Leu Tyr
            980                 985                 990

Ala Asp Ile Ser Ile Ala Lys Pro Glu Lys Ile Ile Lys Leu Ile Arg
            995                 1000                1005

Thr Ser Asn Ser Asn Asn Ser Leu Gly Gln Ile Ile Val Met Asp Ser
        1010                1015                1020

Ile Gly Asn Asn Cys Thr Met Asn Phe Gln Asn Asn Asn Gly Gly Asn
1025                1030                1035                1040

Ile Gly Leu Leu Gly Phe His Ser Asn Asn Leu Val Ala Ser Ser Trp
                1045                1050                1055

Tyr Tyr Asn Asn Ile Arg Lys Asn Thr Ser Ser Asn Gly Cys Phe Trp
            1060                1065                1070

Ser Phe Ile Ser Lys Glu His Gly Trp Gln Glu Asn
        1075                1080
```

<210> SEQ ID NO 9
<211> LENGTH: 229
<212> TYPE: PRT
<213> ORGANISM: Artificial Sequence
<220> FEATURE:
<223> OTHER INFORMATION: Polypeptide comprising a mitochondrial leader
      from human Mn-SOD and Mn-SOD from B. Stearothermophilus

<400> SEQUENCE: 9

```
Met Leu Ser Arg Ala Val Cys Gly Thr Ser Arg Gln Leu Ala Pro Ala
1               5                   10                  15

Leu Gly Tyr Leu Gly Ser Arg Gln Lys His Ser Arg Gly Ser Pro Ala
            20                  25                  30

Leu Pro Tyr Pro Tyr Asp Ala Leu Glu Pro His Ile Asp Lys Glu Thr
        35                  40                  45

Met Asn Ile His His Thr Lys His His Asn Thr Tyr Val Thr Asn Leu
    50                  55                  60

Asn Ala Ala Leu Glu Gly His Pro Asp Leu Gln Asn Lys Ser Leu Glu
65                  70                  75                  80

Glu Leu Leu Ser Asn Leu Glu Ala Leu Pro Glu Ser Ile Arg Thr Ala
                85                  90                  95

Val Arg Asn Asn Gly Gly Gly His Ala Asn His Ser Leu Phe Trp Thr
            100                 105                 110

Ile Leu Ser Pro Asn Gly Gly Gly Glu Pro Thr Gly Glu Leu Ala Asp
        115                 120                 125

Ala Ile Asn Lys Lys Phe Gly Ser Phe Thr Ala Phe Lys Asp Glu Phe
    130                 135                 140

Ser Lys Ala Ala Ala Gly Arg Phe Gly Ser Gly Trp Ala Trp Leu Val
145                 150                 155                 160

Val Asn Asn Gly Glu Leu Glu Ile Thr Ser Thr Pro Asn Gln Asp Ser
                165                 170                 175

Pro Ile Met Glu Gly Lys Thr Pro Ile Leu Gly Leu Asp Val Trp Glu
            180                 185                 190
```

```
-continued

His Ala Tyr Tyr Leu Lys Tyr Gln Asn Arg Arg Pro Glu Tyr Ile Ala
        195                 200                 205

Ala Phe Trp Asn Val Val Asn Trp Asp Glu Val Ala Lys Arg Tyr Ser
    210                 215                 220

Glu Ala Lys Ala Lys
225

<210> SEQ ID NO 10
<211> LENGTH: 24
<212> TYPE: PRT
<213> ORGANISM: Artificial Sequence
<220> FEATURE:
<223> OTHER INFORMATION: Modified human mitocondrial leader sequence

<400> SEQUENCE: 10

Met Leu Ser Arg Ala Val Ser Gly Thr Ser Arg Gln Leu Ala Pro Ala
 1               5                  10                  15

Leu Gly Tyr Leu Gly Ser Arg Gln
                20

<210> SEQ ID NO 11
<211> LENGTH: 24
<212> TYPE: PRT
<213> ORGANISM: Artificial Sequence
<220> FEATURE:
<223> OTHER INFORMATION: Modified human mitochondrial leader sequence

<400> SEQUENCE: 11

Met Leu Ser Arg Ala Val Cys Gly Thr Ser Arg Gln Leu Ala Pro Ala
 1               5                  10                  15

Leu Gly Tyr Leu Gly Ser Arg Gln
                20
```